US008404217B2

(12) United States Patent
Tarara et al.

(10) Patent No.: US 8,404,217 B2
(45) Date of Patent: *Mar. 26, 2013

(54) FORMULATION FOR PULMONARY ADMINISTRATION OF ANTIFUNGAL AGENTS, AND ASSOCIATED METHODS OF MANUFACTURE AND USE

(75) Inventors: Thomas E. Tarara, Burlingame, CA (US); Jeffry G. Weers, Belmont, CA (US); Michael A. Eldon, Redwood City, CA (US); Rangachari Narashimhan, Thornhill (CA); Andrew Clark, Woodside, CA (US)

(73) Assignee: Novartis AG, Basel (CH)

( * ) Notice: Subject to any disclaimer, the term of this patent is extended or adjusted under 35 U.S.C. 154(b) by 2639 days.

This patent is subject to a terminal disclaimer.

(21) Appl. No.: 11/187,757

(22) Filed: Jul. 22, 2005

(65) Prior Publication Data

US 2006/0159625 A1   Jul. 20, 2006

Related U.S. Application Data

(63) Continuation-in-part of application No. 10/032,239, filed on Dec. 21, 2001, now Pat. No. 7,473,433, and a continuation-in-part of application No. 09/851,226, filed on May 8, 2001, now Pat. No. 7,442,388, and a continuation-in-part of application No. 09/568,818,
(Continued)

(51) Int. Cl.
   *A61L 9/04*    (2006.01)
(52) U.S. Cl. .................................................. 424/45
(58) Field of Classification Search .................. None
   See application file for complete search history.

(56) References Cited

U.S. PATENT DOCUMENTS

| | | |
|---|---|---|
| 979,993 A | 10/1910 | O'Byrne et al. |
| 1,855,591 A | 4/1932 | Wallerstein |
| 2,457,036 A | 12/1948 | Epstein |
| 2,797,201 A | 6/1957 | Veatch et al. |
| 3,014,844 A | 12/1961 | Thiel et al. |
| 3,362,405 A | 1/1968 | Hazel |
| 3,555,717 A | 1/1971 | Chivers |
| 3,619,294 A | 11/1971 | Black et al. |
| 3,632,357 A | 1/1972 | Childs |
| 3,655,442 A | 4/1972 | Schwar et al. |
| 3,745,682 A | 7/1973 | Waldeisen |
| 3,812,854 A | 5/1974 | Michaels et al. |
| 3,948,263 A | 4/1976 | Drake, Jr. et al. |
| 3,957,964 A | 5/1976 | Grimm, III |
| 3,964,483 A | 6/1976 | Mathes |
| 3,975,512 A | 8/1976 | Long, Jr. |
| 3,991,761 A | 11/1976 | Cocozza |
| 4,009,280 A | 2/1977 | Macarthur et al. |
| 4,016,254 A | 4/1977 | Saeger |
| 4,027,015 A | 5/1977 | Weinstein et al. |
| 4,036,223 A | 7/1977 | Obert |
| 4,069,819 A | 1/1978 | Valentini et al. |
| 4,089,120 A | 5/1978 | Kozischek |
| 4,098,273 A | 7/1978 | Glenn |
| 4,102,999 A | 7/1978 | Umezawa et al. |
| 4,114,615 A | 9/1978 | Wetterlin |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,161,516 A | 7/1979 | Bell |
| 4,180,593 A | 12/1979 | Cohan |
| 4,201,774 A | 5/1980 | Igarashi et al. |
| 4,211,769 A | 7/1980 | Okada et al. |
| 4,223,130 A | 9/1980 | Weinstein et al. |
| 4,244,949 A | 1/1981 | Gupta |
| 4,247,066 A | 1/1981 | Frost et al. |
| 4,253,468 A | 3/1981 | Lehmbeck |
| 4,281,031 A | 7/1981 | Hillman et al. |
| 4,326,524 A | 4/1982 | Drake, Jr. et al. |
| 4,327,076 A | 4/1982 | Puglia et al. |
| 4,327,077 A | 4/1982 | Puglia et al. |
| 4,338,931 A | 7/1982 | Cavazza |
| 4,358,442 A | 11/1982 | Wirtz-Peitz et al. |
| 4,359,462 A | 11/1982 | Weinstein et al. |
| 4,371,557 A | 2/1983 | Oppy et al. |
| 4,397,799 A | 8/1983 | Edgren et al. |
| 4,404,228 A | 9/1983 | Cloosterman |
| 4,407,786 A | 10/1983 | Drake et al. |
| 4,452,239 A | 6/1984 | Malem |
| 4,484,577 A | 11/1984 | Sackner et al. |
| 4,524,769 A | 6/1985 | Wetterlin et al. |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |

(Continued)

FOREIGN PATENT DOCUMENTS

| | | |
|---|---|---|
| AU | 714998 | 1/1997 |
| AU | 0714998 | 1/1997 |

(Continued)

OTHER PUBLICATIONS

Block (J. Pharm. Sci., 1973, 62 (4), p. 617-621, abstract only.).*

(Continued)

*Primary Examiner* — Shanon A Foley
(74) *Attorney, Agent, or Firm* — Janah & Associates, PC

(57) ABSTRACT

Formulations are provided for pulmonary administration of an antifungal agent to a patient. Methods of using the formulations in the treatment of antifungal infections are also provided, including treatment of pulmonary aspergillosis with amphotericin B-containing formulations. Methods of manufacturing the formulations to achieve optimum properties are provided as well.

21 Claims, No Drawings

Related U.S. Application Data filed on May 10, 2000, now abandoned, and a continuation-in-part of application No. 10/750,934, filed on Dec. 31, 2003, now abandoned, and a continuation-in-part of application No. 09/888,311, filed on Jun. 22, 2001, now abandoned, and a continuation-in-part of application No. 10/751,342, filed on Dec. 31, 2003, and a continuation-in-part of application No. 11/158,332, filed on Jun. 21, 2005, now Pat. No. 7,326,691.

(60) Provisional application No. 60/257,613, filed on Dec. 21, 2000, provisional application No. 60/208,896, filed on Jun. 2, 2000, provisional application No. 60/216,621, filed on Jul. 7, 2000, provisional application No. 60/437,210, filed on Dec. 31, 2002, provisional application No. 60/437,363, filed on Dec. 31, 2002, provisional application No. 60/581,586, filed on Jun. 21, 2004.

(56) References Cited

U.S. PATENT DOCUMENTS

| | | | |
|---|---|---|---|
| 4,659,696 A | 4/1987 | Hirai et al. | |
| 4,663,167 A | 5/1987 | Lopez-Berestein et al. | |
| 4,680,027 A | 7/1987 | Parsons et al. | |
| 4,684,719 A | 8/1987 | Nishikawa et al. | |
| 4,701,417 A | 10/1987 | Portenhauser et al. | |
| 4,713,249 A | 12/1987 | Schröder | |
| 4,721,709 A | 1/1988 | Seth et al. | |
| 4,739,754 A | 4/1988 | Shaner | |
| 4,748,117 A | 5/1988 | Ko et al. | |
| 4,758,583 A | 7/1988 | Cerami et al. | |
| 4,761,400 A | 8/1988 | Doat et al. | |
| 4,762,857 A | 8/1988 | Bollin, Jr. et al. | |
| 4,765,987 A | 8/1988 | Bonte et al. | |
| 4,790,824 A | 12/1988 | Morrow et al. | |
| 4,793,997 A | 12/1988 | Drake et al. | |
| 4,812,444 A | 3/1989 | Mitsuhashi et al. | |
| 4,814,436 A | 3/1989 | Shibata et al. | |
| 4,818,542 A | 4/1989 | DeLuca et al. | |
| 4,819,629 A | 4/1989 | Jonson | |
| 4,822,777 A | 4/1989 | Abra et al. | |
| 4,824,938 A | 4/1989 | Koyama et al. | |
| 4,830,858 A | 5/1989 | Payne et al. | |
| 4,846,876 A | 7/1989 | Draber et al. | |
| 4,847,079 A | 7/1989 | Kwan | |
| 4,851,211 A | 7/1989 | Adjei et al. | |
| 4,855,326 A | 8/1989 | Fuisz | |
| 4,861,627 A | 8/1989 | Mathiowitz et al. | |
| 4,865,871 A | 9/1989 | Livesey et al. | |
| 4,866,051 A | 9/1989 | Hunt et al. | |
| 4,877,619 A | 10/1989 | Richer et al. | |
| 4,883,762 A | 11/1989 | Hoskins | |
| 4,891,319 A | 1/1990 | Roser | |
| 4,895,719 A | 1/1990 | Radhakrishnan et al. | |
| 4,902,789 A | 2/1990 | Michel et al. | |
| 4,904,479 A | 2/1990 | Illum | |
| 4,906,463 A | 3/1990 | Cleary et al. | |
| 4,907,583 A | 3/1990 | Wetterlin et al. | |
| 4,942,544 A | 7/1990 | McIntosh et al. | |
| 4,950,477 A | 8/1990 | Schmitt et al. | |
| 4,952,402 A | 8/1990 | Sparks et al. | |
| 4,971,787 A | 11/1990 | Cherukuri et al. | |
| 4,973,465 A | 11/1990 | Baurain et al. | |
| 4,978,654 A | 12/1990 | Lopez-Berestein et al. | |
| 4,984,158 A | 1/1991 | Hillsman | |
| 4,988,683 A | 1/1991 | Corbiere | |
| 4,995,385 A | 2/1991 | Valentini et al. | |
| 4,999,384 A | 3/1991 | Roberts et al. | |
| 5,006,343 A | 4/1991 | Benson et al. | |
| 5,011,678 A | 4/1991 | Wang et al. | |
| 5,013,557 A | 5/1991 | Tai | |
| 5,017,372 A | 5/1991 | Hastings | |
| 5,026,566 A | 6/1991 | Roser | |
| 5,026,772 A | 6/1991 | Kobayashi et al. | |
| 5,032,582 A | 7/1991 | Abra et al. | |
| 5,032,585 A | 7/1991 | Lichtenberger | |
| 5,033,463 A | 7/1991 | Cocozza | |
| 5,043,158 A | 8/1991 | Sleytr et al. | |
| 5,043,165 A | 8/1991 | Radhakrishnan | |
| 5,049,388 A | 9/1991 | Knight et al. | |
| 5,049,389 A * | 9/1991 | Radhakrishnan | 424/450 |
| 5,069,936 A | 12/1991 | Yen | |
| 5,089,181 A | 2/1992 | Hauser | |
| 5,091,187 A | 2/1992 | Haynes | |
| 5,098,893 A | 3/1992 | Franks et al. | |
| 5,100,591 A | 3/1992 | Leclef et al. | |
| 5,112,596 A | 5/1992 | Malfroy-Camine | |
| 5,112,598 A | 5/1992 | Biesalski | |
| 5,118,494 A | 6/1992 | Schultz et al. | |
| 5,126,123 A | 6/1992 | Johnson | |
| 5,145,684 A | 9/1992 | Liversidge et al. | |
| 5,149,543 A | 9/1992 | Cohen et al. | |
| 5,149,653 A | 9/1992 | Roser | |
| 5,154,930 A | 10/1992 | Popescu et al. | |
| 5,160,745 A | 11/1992 | DeLuca et al. | |
| 5,173,298 A | 12/1992 | Meadows | |
| 5,182,097 A | 1/1993 | Byron et al. | |
| 5,190,029 A | 3/1993 | Byron et al. | |
| 5,194,266 A | 3/1993 | Abra et al. | |
| 5,200,399 A | 4/1993 | Wettlaufer et al. | |
| 5,202,159 A | 4/1993 | Chen et al. | |
| 5,202,333 A | 4/1993 | Berger et al. | |
| 5,204,108 A | 4/1993 | Illum | |
| 5,208,226 A | 5/1993 | Palmer | |
| 5,215,079 A | 6/1993 | Fine et al. | |
| 5,225,183 A | 7/1993 | Purewal et al. | |
| 5,230,884 A | 7/1993 | Evans et al. | |
| 5,239,993 A | 8/1993 | Evans | |
| 5,240,712 A | 8/1993 | Smith et al. | |
| 5,240,843 A | 8/1993 | Gibson et al. | |
| 5,240,846 A | 8/1993 | Collins et al. | |
| 5,254,330 A | 10/1993 | Ganderton et al. | |
| 5,260,306 A | 11/1993 | Boardman et al. | |
| 5,262,405 A | 11/1993 | Girod-Vaquez et al. | |
| 5,270,048 A | 12/1993 | Drake | |
| 5,284,133 A | 2/1994 | Burns et al. | |
| 5,284,656 A | 2/1994 | Platz et al. | |
| 5,290,765 A | 3/1994 | Wettlaufer et al. | |
| 5,299,566 A | 4/1994 | Davis et al. | |
| 5,304,125 A | 4/1994 | Leith | |
| 5,306,483 A | 4/1994 | Mautone | |
| 5,306,506 A | 4/1994 | Zema et al. | |
| 5,308,620 A | 5/1994 | Yen | |
| 5,309,900 A | 5/1994 | Knoch et al. | |
| 5,312,335 A | 5/1994 | McKinnon et al. | |
| 5,312,909 A | 5/1994 | Driessen et al. | |
| 5,340,564 A | 8/1994 | Illig et al. | |
| 5,342,625 A | 8/1994 | Hauer et al. | |
| 5,348,730 A | 9/1994 | Greenleaf et al. | |
| 5,348,852 A | 9/1994 | Bonderman | |
| 5,354,562 A | 10/1994 | Platz et al. | |
| 5,354,934 A | 10/1994 | Pitt et al. | |
| 5,366,734 A | 11/1994 | Hutchinson | |
| 5,376,359 A | 12/1994 | Johnson | |
| 5,380,473 A | 1/1995 | Bogue et al. | |
| 5,380,519 A | 1/1995 | Schneider et al. | |
| 5,384,345 A | 1/1995 | Naton | |
| 5,387,431 A | 2/1995 | Fuisz | |
| 5,389,373 A | 2/1995 | Davis et al. | |
| 5,403,861 A | 4/1995 | Goldin et al. | |
| 5,404,871 A | 4/1995 | Goodman et al. | |
| 5,422,360 A | 6/1995 | Miyajima et al. | |
| 5,422,384 A | 6/1995 | Samuels et al. | |
| 5,425,951 A | 6/1995 | Goodrich, Jr. et al. | |
| 5,437,272 A | 8/1995 | Fuhrman | |
| 5,437,274 A | 8/1995 | Khoobehi et al. | |
| 5,451,569 A | 9/1995 | Wong et al. | |
| 5,453,514 A | 9/1995 | Niigata et al. | |
| 5,458,135 A | 10/1995 | Patton et al. | |
| 5,470,885 A | 11/1995 | Fuhrman et al. | |
| 5,474,059 A | 12/1995 | Cooper | |
| 5,474,759 A | 12/1995 | Fassberg et al. | |

| Patent No. | Date | Inventor(s) | Patent No. | Date | Inventor(s) |
|---|---|---|---|---|---|
| 5,482,927 A | 1/1996 | Maniar et al. | 5,733,555 A | 3/1998 | Chu |
| 5,490,498 A | 2/1996 | Faithfull et al. | 5,735,263 A | 4/1998 | Rubsamen et al. |
| 5,492,688 A | 2/1996 | Byron et al. | 5,736,124 A | 4/1998 | Akehurst et al. |
| 5,506,203 A | 4/1996 | Backstrom et al. | 5,740,064 A | 4/1998 | Witte et al. |
| 5,508,269 A | 4/1996 | Smith et al. | 5,740,794 A | 4/1998 | Smith et al. |
| 5,510,118 A | 4/1996 | Bosch et al. | 5,741,478 A | 4/1998 | Osborne et al. |
| 5,512,547 A | 4/1996 | Johnson et al. | 5,741,522 A | 4/1998 | Violante et al. |
| 5,518,709 A | 5/1996 | Sutton et al. | 5,743,250 A | 4/1998 | Gonda et al. |
| 5,518,731 A | 5/1996 | Meadows | 5,743,252 A | 4/1998 | Rubsamen et al. |
| 5,518,998 A | 5/1996 | Backstrom et al. | 5,744,123 A | 4/1998 | Akehurst et al. |
| 5,527,521 A | 6/1996 | Unger | 5,744,166 A | 4/1998 | Illum |
| 5,534,502 A | 7/1996 | Seki et al. | 5,747,001 A | 5/1998 | Wiedmann et al. |
| 5,540,225 A | 7/1996 | Schutt | 5,747,445 A | 5/1998 | Backstrom et al. |
| 5,542,935 A | 8/1996 | Unger et al. | 5,755,218 A | 5/1998 | Johansson et al. |
| 5,547,656 A | 8/1996 | Unger | 5,756,104 A | 5/1998 | de Haan et al. |
| 5,547,696 A | 8/1996 | Sorenson | 5,759,572 A | 6/1998 | Sugimoto et al. |
| 5,552,160 A | 9/1996 | Liversidge et al. | 5,766,520 A | 6/1998 | Bronshtein |
| 5,560,931 A | 10/1996 | Eickhoff et al. | 5,766,573 A | 6/1998 | Purewal et al. |
| 5,562,608 A | 10/1996 | Sekins et al. | 5,770,187 A | 6/1998 | Hasebe et al. |
| 5,567,439 A | 10/1996 | Mters et al. | 5,770,222 A | 6/1998 | Unger et al. |
| 5,569,448 A | 10/1996 | Wong et al. | 5,770,234 A | 6/1998 | Gristina et al. |
| 5,569,450 A | 10/1996 | Duan et al. | 5,770,559 A | 6/1998 | Manning et al. |
| 5,571,499 A | 11/1996 | Hafler et al. | 5,770,585 A | 6/1998 | Kaufman et al. |
| 5,577,497 A | 11/1996 | Mecikalski et al. | 5,775,320 A | 7/1998 | Patton et al. |
| 5,580,575 A | 12/1996 | Unger et al. | 5,776,496 A | 7/1998 | Violante et al. |
| 5,580,859 A | 12/1996 | Felgner et al. | 5,776,904 A | 7/1998 | Seki et al. |
| 5,589,167 A | 12/1996 | Cleland et al. | 5,780,014 A | 7/1998 | Eljamal et al. |
| 5,591,453 A | 1/1997 | Ducheyne et al. | 5,780,295 A | 7/1998 | Livesey et al. |
| 5,605,673 A | 2/1997 | Schutt et al. | 5,785,049 A | 7/1998 | Smith et al. |
| 5,605,674 A | 2/1997 | Purewal et al. | 5,804,212 A | 9/1998 | Illum |
| 5,607,915 A | 3/1997 | Patton et al. | 5,807,552 A | 9/1998 | Stanton et al. |
| 5,611,344 A | 3/1997 | Bernstein et al. | 5,811,406 A | 9/1998 | Szoka, Jr. et al. |
| 5,612,053 A | 3/1997 | Baichwal et al. | 5,814,607 A | 9/1998 | Patton |
| 5,616,311 A | 4/1997 | Yen | 5,817,293 A | 10/1998 | Akehurst et al. |
| 5,618,786 A | 4/1997 | Roosdorp et al. | 5,820,883 A | 10/1998 | Tice et al. |
| 5,619,985 A | 4/1997 | Ohki et al. | 5,829,435 A | 11/1998 | Rubsamen et al. |
| 5,621,094 A | 4/1997 | Roser et al. | 5,830,430 A | 11/1998 | Unger et al. |
| 5,631,225 A | 5/1997 | Sorensen | 5,830,853 A | 11/1998 | Backstrom et al. |
| 5,635,159 A | 6/1997 | Fu Lu et al. | 5,849,700 A | 12/1998 | Sorensen et al. |
| 5,635,161 A | 6/1997 | Adjei et al. | 5,851,453 A | 12/1998 | Hanna et al. |
| 5,642,728 A | 7/1997 | Andersson et al. | 5,853,698 A | 12/1998 | Straub et al. |
| 5,648,095 A | 7/1997 | Illum et al. | 5,853,740 A | 12/1998 | Lu et al. |
| 5,653,961 A | 8/1997 | McNally et al. | 5,853,752 A | 12/1998 | Unger et al. |
| 5,653,962 A | 8/1997 | Akehurst et al. | 5,853,763 A | 12/1998 | Tice et al. |
| 5,654,007 A | 8/1997 | Johnson et al. | 5,855,913 A | 1/1999 | Hanes et al. |
| 5,654,278 A | 8/1997 | Sorenson | 5,856,367 A | 1/1999 | Barrows et al. |
| 5,655,521 A | 8/1997 | Faithfull et al. | 5,858,410 A | 1/1999 | Muller et al. |
| 5,656,297 A | 8/1997 | Bernstein et al. | 5,858,784 A | 1/1999 | Debs et al. |
| 5,658,549 A | 8/1997 | Akehurst et al. | 5,861,175 A | 1/1999 | Walters et al. |
| 5,659,297 A | 8/1997 | Tatavoosian | 5,863,554 A | 1/1999 | Illum |
| 5,667,808 A | 9/1997 | Johnson et al. | 5,873,360 A | 2/1999 | Davies et al. |
| 5,667,809 A | 9/1997 | Trevino et al. | 5,874,063 A | 2/1999 | Briggner et al. |
| 5,673,686 A | 10/1997 | Villax et al. | 5,874,064 A | 2/1999 | Edwards et al. |
| 5,674,471 A | 10/1997 | Akehurst et al. | 5,875,776 A | 3/1999 | Vaghefi |
| 5,674,472 A | 10/1997 | Akehurst et al. | 5,891,844 A | 4/1999 | Hafner |
| 5,674,473 A | 10/1997 | Purewal et al. | 5,891,873 A | 4/1999 | Colaco et al. |
| 5,676,929 A | 10/1997 | Akehurst et al. | 5,898,028 A | 4/1999 | Jensen et al. |
| 5,676,931 A | 10/1997 | Adjei et al. | 5,921,447 A | 7/1999 | Barger et al. |
| 5,681,545 A | 10/1997 | Purewal et al. | 5,925,334 A | 7/1999 | Rubin et al. |
| 5,681,746 A | 10/1997 | Bodner et al. | 5,928,469 A | 7/1999 | Franks et al. |
| 5,683,676 A | 11/1997 | Akehurst et al. | 5,928,647 A | 7/1999 | Rock |
| 5,683,677 A | 11/1997 | Purewal et al. | 5,934,273 A | 8/1999 | Andersson et al. |
| 5,688,782 A | 11/1997 | Neale et al. | 5,948,411 A | 9/1999 | Koyama et al. |
| 5,690,954 A | 11/1997 | Illum | 5,955,143 A | 9/1999 | Wheatley et al. |
| 5,695,743 A | 12/1997 | Purewal et al. | 5,955,448 A | 9/1999 | Colaco et al. |
| 5,695,744 A | 12/1997 | Neale et al. | 5,962,424 A * | 10/1999 | Hallahan et al. ............ 514/44 R |
| 5,698,537 A | 12/1997 | Pruss | 5,965,156 A | 10/1999 | Proffitt et al. |
| 5,705,482 A | 1/1998 | Christensen et al. | 5,972,366 A | 10/1999 | Haynes et al. |
| 5,707,352 A | 1/1998 | Sekins et al. | 5,972,388 A | 10/1998 | Sakon et al. |
| 5,707,644 A | 1/1998 | Illum | 5,976,436 A | 11/1999 | Livesley et al. |
| 5,714,141 A | 2/1998 | Ho et al. | 5,976,574 A | 11/1999 | Gordon |
| 5,718,222 A | 2/1998 | Lloyd et al. | 5,977,081 A | 11/1999 | Marciani |
| 5,718,921 A | 2/1998 | Mathiowitz et al. | 5,985,248 A | 11/1999 | Gordon et al. |
| 5,720,940 A | 2/1998 | Purewal et al. | 5,985,309 A | 11/1999 | Edwards et al. |
| 5,724,957 A | 3/1998 | Rubsamen et al. | 5,989,583 A | 11/1999 | Amselem et al. |
| 5,725,841 A | 3/1998 | Duan et al. | 5,993,783 A | 11/1999 | Eljamal et al. |
| 5,725,871 A | 3/1998 | Illum | 5,993,805 A | 11/1999 | Sutton et al. |
| 5,727,546 A | 3/1998 | Clarke et al. | 5,994,314 A | 11/1999 | Eljamal et al. |
| 5,728,574 A | 3/1998 | Legg | 5,994,318 A | 11/1999 | Gould-Fogerite et al. |

| | | |
|---|---|---|
| 5,997,848 A | 12/1999 | Patton |
| 6,001,336 A | 12/1999 | Gordon |
| 6,013,638 A | 1/2000 | Crystal et al. |
| 6,017,310 A | 1/2000 | Johnson et al. |
| 6,019,968 A | 2/2000 | Platz et al. |
| 6,032,666 A | 3/2000 | Davies et al. |
| 6,034,080 A | 3/2000 | Colaco et al. |
| 6,041,777 A | 3/2000 | Faithfull et al. |
| 6,048,546 A | 4/2000 | Sasaki et al. |
| 6,051,256 A | 4/2000 | Platz et al. |
| 6,051,259 A | 4/2000 | Johnson et al. |
| 6,051,566 A | 4/2000 | Bianco |
| 6,060,069 A | 5/2000 | Hill et al. |
| 6,068,600 A | 5/2000 | Johnson et al. |
| 6,071,428 A | 6/2000 | Franks et al. |
| 6,071,497 A | 6/2000 | Steiner et al. |
| 6,077,543 A | 6/2000 | Gordon et al. |
| 6,086,376 A | 7/2000 | Moussa et al. |
| 6,113,948 A | 9/2000 | Heath et al. |
| 6,116,237 A | 9/2000 | Schultz et al. |
| 6,117,455 A | 9/2000 | Takada et al. |
| 6,120,751 A | 9/2000 | Unger |
| 6,123,924 A | 9/2000 | Mistry et al. |
| 6,123,936 A | 9/2000 | Platz et al. |
| 6,129,934 A | 10/2000 | Egan et al. |
| 6,136,295 A | 10/2000 | Edwards et al. |
| 6,136,346 A | 10/2000 | Eljamal et al. |
| 6,138,668 A | 10/2000 | Patton et al. |
| 6,139,819 A | 10/2000 | Unger et al. |
| 6,142,216 A | 11/2000 | Lannes |
| 6,143,276 A | 11/2000 | Unger |
| 6,165,463 A | 12/2000 | Platz et al. |
| 6,165,508 A | 12/2000 | Tracy et al. |
| 6,165,597 A | 12/2000 | Williams et al. |
| 6,180,136 B1 | 1/2001 | Larson et al. |
| RE37,053 E | 2/2001 | Hanes et al. |
| 6,187,344 B1 | 2/2001 | Eljamal et al. |
| 6,190,859 B1 | 2/2001 | Putnak et al. |
| 6,207,135 B1 | 3/2001 | Rossling et al. |
| 6,207,703 B1 | 3/2001 | Ponikau |
| 6,215,019 B1 | 4/2001 | Pederson et al. |
| 6,230,707 B1 | 5/2001 | Horlin |
| 6,231,851 B1 | 5/2001 | Platz et al. |
| 6,248,720 B1 | 6/2001 | Mathiowitz et al. |
| 6,254,854 B1 | 7/2001 | Edwards et al. |
| 6,257,233 B1 | 7/2001 | Burr et al. |
| 6,258,341 B1 | 7/2001 | Foster et al. |
| 6,284,282 B1 | 9/2001 | Maa et al. |
| 6,290,991 B1 | 9/2001 | Roser et al. |
| 6,303,581 B2 | 10/2001 | Pearlman |
| 6,303,582 B1 | 10/2001 | Eljamal et al. |
| 6,309,623 B1 | 10/2001 | Weers et al. |
| 6,309,671 B1 | 10/2001 | Foster et al. |
| 6,313,102 B1 | 11/2001 | Colaco et al. |
| 6,315,983 B1 | 11/2001 | Eistetter |
| 6,331,310 B1 | 12/2001 | Roser et al. |
| 6,334,182 B2 | 12/2001 | Merchant et al. |
| 6,357,490 B1 | 3/2002 | Johnston et al. |
| 6,358,530 B1 | 3/2002 | Eljamal et al. |
| 6,365,190 B1 | 4/2002 | Gordon et al. |
| 6,372,258 B1 | 4/2002 | Platz et al. |
| 6,383,471 B1 | 5/2002 | Chen et al. |
| 6,387,886 B1 | 5/2002 | Montgomery et al. |
| 6,416,739 B1 | 7/2002 | Rogerson et al. |
| 6,422,338 B1 | 7/2002 | Menzel et al. |
| 6,423,334 B1 | 7/2002 | Brayden et al. |
| 6,423,338 B1 | 7/2002 | Larson et al. |
| 6,423,344 B1 | 7/2002 | Platz et al. |
| 6,426,210 B1 | 7/2002 | Franks et al. |
| 6,433,040 B1 | 8/2002 | Dellamary et al. |
| 6,468,782 B1 | 10/2002 | Tunnacliffe et al. |
| 6,475,468 B2 | 11/2002 | Zhu et al. |
| 6,479,049 B1 | 11/2002 | Platz et al. |
| 6,503,411 B1 | 1/2003 | Franks et al. |
| 6,503,480 B1 | 1/2003 | Edwards et al. |
| 6,509,006 B1 | 1/2003 | Platz et al. |
| 6,514,482 B1 | 2/2003 | Bartus et al. |
| 6,514,496 B1 | 2/2003 | Platz et al. |
| 6,518,239 B1 | 2/2003 | Kuo et al. |

| | | |
|---|---|---|
| 6,546,929 B2 | 4/2003 | Burr et al. |
| 6,551,578 B2 | 4/2003 | Adjei et al. |
| 6,565,871 B2 | 5/2003 | Roser et al. |
| 6,565,885 B1 | 5/2003 | Tarara et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,592,904 B2 | 7/2003 | Platz et al. |
| 6,613,352 B2 | 9/2003 | Lagace et al. |
| 6,630,169 B1 | 10/2003 | Bot et al. |
| 6,638,495 B2 | 10/2003 | Weers et al. |
| 6,649,911 B2 | 11/2003 | Kawato |
| 6,652,837 B1 | 11/2003 | Edwards et al. |
| 6,655,379 B2 | 12/2003 | Clark et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,696,597 B2 | 2/2004 | Pederson et al. |
| 6,737,045 B2 | 5/2004 | Patton et al. |
| 6,737,066 B1 | 5/2004 | Moss |
| 6,752,893 B2 | 6/2004 | Frieder et al. |
| 6,797,258 B2 | 9/2004 | Platz et al. |
| 6,811,792 B2 | 11/2004 | Roser et al. |
| 6,825,031 B2 | 11/2004 | Franks et al. |
| 6,893,657 B2 | 5/2005 | Roser et al. |
| 6,921,527 B2 | 7/2005 | Platz et al. |
| 6,946,117 B1 | 9/2005 | Schutt et al. |
| 7,306,787 B2 | 12/2007 | Tarara et al. |
| 7,393,544 B2 | 7/2008 | Dellamary et al. |
| 7,442,388 B2 * | 10/2008 | Weers et al. .................. 424/489 |
| 2001/0035184 A1 | 11/2001 | Schuler et al. |
| 2002/0017295 A1 | 2/2002 | Weers et al. |
| 2002/0037316 A1 | 3/2002 | Weers et al. |
| 2002/0052310 A1 | 5/2002 | Edwards et al. |
| 2002/0127188 A1 | 9/2002 | Platz et al. |
| 2002/0132787 A1 | 9/2002 | Eljamal et al. |
| 2002/0177562 A1 | 11/2002 | Weickert et al. |
| 2002/0187106 A1 | 12/2002 | Weers et al. |
| 2002/0192164 A1 | 12/2002 | Patton et al. |
| 2003/0035778 A1 | 2/2003 | Platz et al. |
| 2003/0068277 A1 | 4/2003 | Vanbever et al. |
| 2003/0068279 A1 | 4/2003 | Platz et al. |
| 2003/0072718 A1 | 4/2003 | Platz et al. |
| 2003/0086877 A1 | 5/2003 | Platz et al. |
| 2003/0092666 A1 | 5/2003 | Eljamal et al. |
| 2003/0096774 A1 | 5/2003 | Gonda et al. |
| 2003/0113273 A1 | 6/2003 | Patton et al. |
| 2003/0113900 A1 | 6/2003 | Tunnacliff et al. |
| 2003/0171282 A1 | 9/2003 | Patton |
| 2003/0185765 A1 | 10/2003 | Platz et al. |
| 2003/0198601 A1 | 10/2003 | Platz et al. |
| 2003/0203036 A1 | 10/2003 | Gordon et al. |
| 2003/0215512 A1 | 11/2003 | Foster et al. |
| 2003/0215514 A1 | 11/2003 | Platz et al. |
| 2003/0219490 A1 | 11/2003 | Hovey et al. |
| 2004/0052825 A1 | 3/2004 | Roser et al. |
| 2004/0096400 A1 | 5/2004 | Patton et al. |
| 2004/0096401 A1 | 5/2004 | Patton et al. |
| 2004/0105820 A1 | 6/2004 | Weers et al. |
| 2004/0156792 A1 | 8/2004 | Tarara et al. |
| 2004/0170568 A1 | 9/2004 | Weers et al. |
| 2004/0176391 A1 | 9/2004 | Weers et al. |
| 2004/0219206 A1 | 11/2004 | Roser et al. |
| 2005/0074449 A1 | 4/2005 | Bot et al. |
| 2005/0147566 A1 | 7/2005 | Fleming et al. |
| 2005/0186143 A1 | 8/2005 | Stevenson et al. |
| 2005/0203002 A1 | 9/2005 | Tzannis et al. |
| 2005/0214224 A1 | 9/2005 | Weers et al. |
| 2006/0159625 A1 | 7/2006 | Tarara et al. |
| 2006/0159629 A1 | 7/2006 | Tarara et al. |
| 2006/0165606 A1 | 7/2006 | Tarara et al. |

FOREIGN PATENT DOCUMENTS

| | | |
|---|---|---|
| AU | 757337 | 2/2003 |
| AU | 731671 | 4/2004 |
| BE | 0902257 | 8/1985 |
| CA | 2036844 | 8/1991 |
| CA | 2136704 | 5/1995 |
| DE | 0161072 | 10/1904 |
| DE | 0471490 | 8/1931 |
| DE | 1080265 | 4/1960 |
| DE | 3141498 | 4/1983 |
| DE | 3713326 | 10/1987 |
| DE | 19616573 | 11/1997 |
| EP | 0015123 | 3/1980 |
| EP | 0072046 | 2/1983 |
| EP | 0090356 | 10/1983 |
| EP | 0111216 | 6/1984 |
| EP | 0136030 | 4/1985 |
| EP | 0139286 | 5/1985 |
| EP | 0140489 | 5/1985 |
| EP | 0222313 | 5/1987 |
| EP | 0229810 | 7/1987 |
| EP | 0274431 | 7/1988 |
| EP | 0282179 | 9/1988 |
| EP | 0325936 | 8/1989 |
| EP | 0356154 | 2/1990 |
| EP | 0360340 | 3/1990 |
| EP | 0366303 | 5/1990 |
| EP | 0372777 | 6/1990 |
| EP | 0383569 | 8/1990 |
| EP | 0415567 | 3/1991 |
| EP | 0174759 | 4/1991 |
| EP | 0430045 | 6/1991 |
| EP | 0433679 | 6/1991 |
| EP | 0463653 | 1/1992 |
| EP | 0474874 | 3/1992 |
| EP | 0520748 | 10/1992 |
| EP | 0391896 | 3/1994 |
| EP | 0536204 | 4/1994 |
| EP | 0600730 | 8/1994 |
| EP | 0611567 | 8/1994 |
| EP | 0616524 | 9/1994 |
| EP | 0553298 | 11/1994 |
| EP | 634166 | 1/1995 |
| EP | 0640347 | 3/1995 |
| EP | 0653205 | 5/1995 |
| EP | 0655237 | 5/1995 |
| EP | 0656203 | 6/1995 |
| EP | 0656205 | 6/1995 |
| EP | 0656206 | 6/1995 |
| EP | 0658101 | 6/1995 |
| EP | 0513127 | 7/1995 |
| EP | 0663840 | 7/1995 |
| EP | 0493437 | 8/1995 |
| EP | 0556256 | 8/1995 |
| EP | 0616525 | 9/1995 |
| EP | 0499344 | 10/1995 |
| EP | 0681843 | 11/1995 |
| EP | 0587790 | 1/1996 |
| EP | 0605578 | 1/1996 |
| EP | 0588897 | 2/1996 |
| EP | 0714905 | 6/1996 |
| EP | 0743860 | 11/1996 |
| EP | 0536235 | 1/1997 |
| EP | 0773781 | 5/1997 |
| EP | 0257956 | 3/1998 |
| EP | 0539522 | 12/1998 |
| EP | 0904056 | 3/1999 |
| EP | 1019022 | 4/2003 |
| ES | 8403520 | 6/1984 |
| FR | 2238476 | 2/1975 |
| GB | 1263780 | 2/1972 |
| GB | 1265615 | 3/1972 |
| GB | 1288094 | 9/1972 |
| GB | 1381588 | 1/1975 |
| GB | 1477775 | 6/1977 |
| GB | 1533012 | 11/1978 |
| GB | 2025196 | 1/1980 |
| GB | 2065659 | 7/1981 |
| GB | 2105189 | 3/1983 |
| GB | 2126588 | 9/1984 |
| GB | 21878191 | 1/1987 |
| GB | 2237510 | 5/1991 |
| JP | 52139789 | 11/1977 |
| JP | 58216695 | 12/1983 |
| JP | 59095885 | 6/1984 |
| JP | 60244288 | 12/1985 |
| JP | 62228272 | 10/1987 |
| JP | 62255434 | 11/1987 |
| JP | 02084401 | 3/1990 |
| JP | 03038592 | 2/1991 |
| JP | 03264537 | 11/1991 |
| JP | 06100464 | 4/1994 |
| RU | 91263780 | 12/1991 |
| RU | 92025196 | 6/1992 |
| RU | 93008753 | 5/1993 |
| WO | WO8604095 | 7/1986 |
| WO | WO8700196 | 1/1987 |
| WO | WO8702038 | 4/1987 |
| WO | WO8705300 | 9/1987 |
| WO | WO8801862 | 3/1988 |
| WO | WO 88/06450 | 9/1988 |
| WO | WO 88/07853 | 10/1988 |
| WO | WO8808298 | 11/1988 |
| WO | WO8906976 | 8/1989 |
| WO | WO8908449 | 9/1989 |
| WO | WO 90/01873 | 3/1990 |
| WO | WO9005182 | 5/1990 |
| WO | WO 90/06775 | 6/1990 |
| WO | WO 90/11754 | 10/1990 |
| WO | WO9011756 | 10/1990 |
| WO | WO9013285 | 11/1990 |
| WO | WO9015635 | 12/1990 |
| WO | WO9104011 | 4/1991 |
| WO | WO9104715 | 4/1991 |
| WO | WO9106282 | 5/1991 |
| WO | WO9111173 | 8/1991 |
| WO | WO9112823 | 9/1991 |
| WO | WO 91/16444 | 10/1991 |
| WO | WO9116038 | 10/1991 |
| WO | WO9116882 | 11/1991 |
| WO | WO9118091 | 11/1991 |
| WO | WO9200107 | 1/1992 |
| WO | WO9202133 | 2/1992 |
| WO | WO9211050 | 7/1992 |
| WO | WO9214444 | 9/1992 |
| WO | WO9218164 | 10/1992 |
| WO | WO9219243 | 11/1992 |
| WO | WO9300951 | 1/1993 |
| WO | WO 93/03737 | 3/1993 |
| WO | WO9309832 | 5/1993 |
| WO | WO9310758 | 6/1993 |
| WO | WO9311743 | 6/1993 |
| WO | WO9311744 | 6/1993 |
| WO | WO9311745 | 6/1993 |
| WO | WO9311746 | 6/1993 |
| WO | WO9312240 | 6/1993 |
| WO | WO9313752 | 7/1993 |
| WO | WO9314172 | 7/1993 |
| WO | WO9317663 | 9/1993 |
| WO | WO9323065 | 11/1993 |
| WO | WO9323110 | 11/1993 |
| WO | WO9404133 | 3/1994 |
| WO | WO9407514 | 4/1994 |
| WO | WO9408552 | 4/1994 |
| WO | WO9408627 | 4/1994 |
| WO | WO9413271 | 6/1994 |
| WO | WO9422423 | 10/1994 |
| WO | WO9424263 | 10/1994 |
| WO | WO 95/01221 | 1/1995 |
| WO | WO9500127 | 1/1995 |
| WO | WO9500128 | 1/1995 |
| WO | WO9501324 | 1/1995 |
| WO | WO9505194 | 2/1995 |
| WO | WO9506126 | 3/1995 |
| WO | WO9515118 | 6/1995 |
| WO | WO9517195 | 6/1995 |
| WO | WO9520979 | 8/1995 |
| WO | WO 95/24183 | 9/1995 |

| | | |
|---|---|---|
| WO | WO9523613 | 9/1995 |
| WO | WO9524892 | 9/1995 |
| WO | WO9527476 | 10/1995 |
| WO | WO 95/31479 | 11/1995 |
| WO | WO9528944 | 11/1995 |
| WO | WO9531182 | 11/1995 |
| WO | WO9531479 | 11/1995 |
| WO | WO9531964 | 11/1995 |
| WO | WO9533488 | 12/1995 |
| WO | WO 96/00610 | 1/1996 |
| WO | WO9603116 | 2/1996 |
| WO | WO9603978 | 2/1996 |
| WO | WO9609085 | 3/1996 |
| WO | WO9607399 | 4/1996 |
| WO | WO9609814 | 4/1996 |
| WO | WO9615814 | 5/1996 |
| WO | WO9611745 | 6/1996 |
| WO | WO9618388 | 6/1996 |
| WO | WO9619197 | 6/1996 |
| WO | WO9619198 | 6/1996 |
| WO | WO9619199 | 6/1996 |
| WO | WO9619968 | 7/1996 |
| WO | WO9626746 | 9/1996 |
| WO | WO9627393 | 9/1996 |
| WO | WO 96/32096 | 10/1996 |
| WO | WO 96/32149 | 10/1996 |
| WO | WO9632096 | 10/1996 |
| WO | WO9632116 | 10/1996 |
| WO | WO9632149 | 10/1996 |
| WO | WO9636314 | 11/1996 |
| WO | WO9640049 | 12/1996 |
| WO | WO9640066 | 12/1996 |
| WO | WO9640068 | 12/1996 |
| WO | WO9640077 | 12/1996 |
| WO | WO9640277 | 12/1996 |
| WO | WO9640285 | 12/1996 |
| WO | WO 97/03649 | 2/1997 |
| WO | WO9703649 | 2/1997 |
| WO | WO9713503 | 4/1997 |
| WO | WO9725086 | 7/1997 |
| WO | WO9726863 | 7/1997 |
| WO | WO9732609 | 9/1997 |
| WO | WO9734689 | 9/1997 |
| WO | WO 97/36577 | 10/1997 |
| WO | WO9735562 | 10/1997 |
| WO | WO9736574 | 10/1997 |
| WO | WO9736578 | 10/1997 |
| WO | WO9740819 | 11/1997 |
| WO | WO9741833 | 11/1997 |
| WO | WO9744012 | 11/1997 |
| WO | WO9744013 | 11/1997 |
| WO | WO 97/48278 | 12/1997 |
| WO | WO9800111 | 1/1998 |
| WO | WO9801161 | 1/1998 |
| WO | WO9805302 | 2/1998 |
| WO | WO9807414 | 2/1998 |
| WO | WO9808519 | 3/1998 |
| WO | WO9813031 | 4/1998 |
| WO | WO9816205 | 4/1998 |
| WO | WO9817257 | 4/1998 |
| WO | WO9824882 | 6/1998 |
| WO | WO9829096 | 7/1998 |
| WO | WO9829097 | 7/1998 |
| WO | WO9829098 | 7/1998 |
| WO | WO9829099 | 7/1998 |
| WO | WO9829140 | 7/1998 |
| WO | WO9830207 | 7/1998 |
| WO | WO9831346 | 7/1998 |
| WO | WO 98/36825 | 8/1998 |
| WO | WO9833480 | 8/1998 |
| WO | WO9833487 | 8/1998 |
| WO | WO9841188 | 9/1998 |
| WO | WO9851282 | 11/1998 |
| WO | WO 98/55148 | 12/1998 |
| WO | WO9858989 | 12/1998 |
| WO | WO 99/00113 | 1/1999 |
| WO | WO9906026 | 2/1999 |
| WO | WO9909956 | 3/1999 |
| WO | WO 99/16419 | 4/1999 |
| WO | WO 99/16420 | 4/1999 |
| WO | WO 99/16421 | 4/1999 |
| WO | WO 99/16422 | * 4/1999 |
| WO | WO 99/20261 | 4/1999 |
| WO | WO9916419 | 4/1999 |
| WO | WO9916420 | 4/1999 |
| WO | WO9916421 | 4/1999 |
| WO | WO9916422 | 4/1999 |
| WO | WO9932083 | 7/1999 |
| WO | WO9932098 | 7/1999 |
| WO | WO9938493 | 8/1999 |
| WO | WO 99/44594 | 9/1999 |
| WO | WO9944583 | 9/1999 |
| WO | WO9945986 | 9/1999 |
| WO | WO9945987 | 9/1999 |
| WO | WO9947196 | 9/1999 |
| WO | WO 99/61003 | 12/1999 |
| WO | WO9966903 | 12/1999 |
| WO | WO00/01365 | 1/2000 |
| WO | WO0000176 | 1/2000 |
| WO | WO0000215 | 1/2000 |
| WO | WO 00/06184 | 2/2000 |
| WO | WO 00/07572 | 2/2000 |
| WO | WO0010541 | 3/2000 |
| WO | WO0021594 | 4/2000 |
| WO | WO 00/27359 | 5/2000 |
| WO | WO0056262 | 9/2000 |
| WO | WO 00/61178 | 10/2000 |
| WO | WO0061157 | 10/2000 |
| WO | WO 00/72827 | 12/2000 |
| WO | WO 00/72904 | 12/2000 |
| WO | WO0072904 | 12/2000 |
| WO | WO 01/02024 | 1/2001 |
| WO | WO 01/05379 | 1/2001 |
| WO | WO0100263 | 1/2001 |
| WO | WO 01/13927 | 3/2001 |
| WO | WO 01/13956 | 3/2001 |
| WO | WO0113891 | 3/2001 |
| WO | WO0113892 | 3/2001 |
| WO | WO0126683 | 4/2001 |
| WO | WO 01/32144 | 5/2001 |
| WO | WO0132144 | 5/2001 |
| WO | WO0164254 | 9/2001 |
| WO | WO 01/85136 | 11/2001 |
| WO | WO 01/85137 | 11/2001 |
| WO | WO0185136 | 11/2001 |
| WO | WO0185137 | 11/2001 |
| WO | WO0187278 | 11/2001 |
| WO | WO0195874 | 12/2001 |
| WO | WO 02/067902 | 9/2002 |
| WO | WO 02/083220 | 10/2002 |
| WO | WO 2006/002140 | * 1/2006 |
| WO | WO2006002140 | 1/2006 |

OTHER PUBLICATIONS

Cicogna et al. (Antimicrobial Agents and Chemotherapy, 1997, 41 (2), p. 259-261).*
Allen et al., "Prophylactic efficacy of aerosolized liposomal (Ambisome) and non-liposomal (Fungizone) amphotericin B in murine pulmonary aspergillosis," J. Antimicrob. Chemother. (1994) 34:1001-1013.
Beyer et al., "Use of amphotericin B aerosols for the prevention of pulmonary aspergillosis," (1994) 22:143-148.
Calvo et al., "Antifungal prophylaxis during the early postoperative period of lung transplantation," Chest (1999) 115:1301-1304.
Conneally et al., "Nebulized amphotericin B as prophylaxis against invasive aspergillosis in granulocytopenic patients," Bone Marrow Transplant. (1990) 5:403-406.
Cross, "Amphotericin B aerosol for transiently immunocompromised hosts," Chest (1995) 8:599-601.
Diot et al., "Deposition of amphotericin B aerosols in pulmonary aspergilloma," Eur. Respir. J. (1995) 8:1263-1268.
Dubois et al., "The physiologic effects of inhaled amphotericin B," Chest (1995) 108:750-753.
Georgiev et al., "Treatment and development therapeutics in aspergillosis 1. Amphotericin B and its derivatives," Respiration (1992) 59:291-302.

Gilbert et al., "Aerosolized liposomal amphotericin B for treatment of pulmonary and systemic *Cryptococcus neoformans* infection in mice," Antimicrob. Agents Chemother. (1992) 36:1466-1471.

Kim et al., "Preparation by spray drying of amphotericin B-phospholipid composite particles and their anticellular activity," Drug Delivery (2001) 8:143-147.

Palmer et al., "Candidal anastomotic infection in lung transplant recipients," J. Heart Lung Transplant. (1988) 17:1029-1033.

Reichenspurner et al., "Significant reduction in the number of fungal infections after lung, heart-lung, and heart transplantation using aerosolized amphotericin B prophylaxis," Transplant. Proc. (1997) 29:627-628.

Roth et al., "Production of Hollow Spheres," Pergamon Press, vol. 19, pp. 939-942, 1988.
Schwartz et al., "Aerosolized amphotericin B inhalations as prophylaxis of invasive *Aspergillus* infections during prolonged neutropenia: results of a prospective randomized multicenter trial," Blood (1999) 93:3654-3661.
Stevens et al., "A randomized trial of itraconazole in allergic bronchopulmonary aspergillosis," N.Engl. J. Med. (2000) 342:756-762.
Weers et al., "Dispersible powders for inhalation applications: The poor powder dispersibility found with current DPI and Pmdi formulations of micronised drugs can be overcome through the use of Pulmosphere™ technology," Innov. Phannac. Tech. (2000) 1:111-116.
Erjavec et al., "Tolerance and efficacy of amphotericin B inhalations for prevention of invasive pulmonary asperillosis in haematological patients," Eur. J. Clin. Infect Dis. (1997) 16:364-368.
Hertenstein et al, "Low incidence of invasive fungal infections after bone marrow transplantation in patients receiving amphotericin B inhalations during neutropenia," Ann. Hematol. (1994) 68:21-26.
Ruijgrok et al., "Efficacy of aerosolized amphotericin B desoxycholate and liposomal amphotericin B in the treatment of invasive pulmonary aspergillosis in severely immuocompromised rats," J. Antimicrob. Chemother. (2001) 48:89-95.
Shah and Misra, "Development of liposomal amphotericin B dry powder inhaler formulation," Drug. Deliv. (2004) 11:247-253.
U.S. Appl. No. 60/060,337, filed Sep. 1997, Kabalnov.
"Albuterol", Merck Index, 12th edition, edited by Susan Budavari, 1996, monograph 217, p. 40-1.
"Amphotericin B", Merck Index, 12th edition, edited by Susan Budavari, 1996, monograph 627, p. 99.
"Estradiol", Merck Index, 12th edition, edited by Susan Budavari, 1996, monograph 3746, p. 630-1.
"Aerosols, Metered-Dose Inhalers, and Dry Powder Inhalers", Pharmacopeial Previews, 22(6): 3065 (1996).
"Chapter 89—Oral Solid Dosage Forms, "In *Remington's Pharmaceutical Sciences*, 18th Edition, Mack Publishing Co., Gennaro, A.R., pp. 1646-1647 (1990).
"Pfizer and Inhale Therapeutic Systems Enter Pulmonary Insulin Collaboration for Dry Powder Aerosol Delivery", Health News Daily, vol. 7, No. 13, pp. 4-5 (Jan. 1995).
Adjei et al., "Pulmonary Delivery of Peptide Drucs: Effecti of Particle Size on Bioavailability of Leuprolide Acetate in Healthy Male Volunteers", Jun. 1990, Pharmaceutical Research, 7(6), pp. 565-569).
Advertisement for "Stop 'n Grow" manufactured by The Mentholatum Co. Ltd., East Kilbride, Scotland G74 5P3.
Agrimi, U., et al. "Amyloid, Amyloid-Inducers, Cytokines and Heavy Metals in Scrapie and Other Human and Animal Subacute Spongiform Encephalopathies: Some Hypotheses", *Med. Hypotheses*, 40(2): 113-116 (1993).
Ahlneck et al. "The Molecular Basis of Moisture Effects on the Physical and Chemical Stability of Drugs in the Solid State" Int. J. of Pharmaceutics 62: 87-95 (1990).
Akers, M.J., et al., "Glycine Crystallization During Freezing: The Effects of Salt Form, pH, and Ionic Strenght", *Pharmaceutical Research* 12(10):1457-1461 (1995).
Akoh, et al., "One-stage synthesis of raffinose fatty acid polyesters", J. Food Sci., 52:1570-1576 (1987).
Alberts, B., et al., *Molecular Biology of the Cell*, 2nd ed., Garland Publishing, Inc., Ch.2, p. 58 (1989).
Aldous, et al., "The Crystallization of Hydrates from Amorphous Carbohydrates", *Cryo-Letters*, 16:181-186 (1995).
Allen, D.J., et al. "Determination of the Degree of Crystallinity in Solid-Solid Equilibria", J. Pharm. Sci., 58:1190-1193 (1969).
Allison, S.D. and Anchordoquy, Thomas J., *Lyophilization of Nonviral Gene Delivery Systems*, Methods in Molecular Medicine, Nonviral Vectors for Gene Therapy, Ch. 18, pp. 225-252 (Mark A. Findeis ed., Humana Press, 2001).
Allison, S.D., et al., "Mechanisms of Protection of Cationic Lipid-DNA Complexes During Lyophilization", *Journal of Pharmaceutical Sciences* 89(5): 682-691 (2000).
Alonso, "Determinants of Release Rate of Tetanus Vaccine from Polyester Microspheres", Pharm. Res., p. 945-953.
Altenbach et al. "Ca2+ Binding to Phosphatidycholine Bilayers As Studied by Deuterium Magnetic Resonance. Evidence for the Formation of a Ca2+Complex with Two Phospholipid Molecules" Biochemistry 23: 3913-3920 (1984).
Amidon, G.E., et al., "Powder Flow Testing in Preformulation and Formulation Development", *Pharm. Manuf.*, 2: 20-31 (1985).
Amselem, "Polymeric Bigdegradable Lipospheres as Vaccine Delivery Systems,", Poly. For Adv. Tech., p. 351-357.
Anchoroquy, Thomas J., Physical Stabilization of DNA Based Therapeutics, 6(9): DDT 463-470 (May 2001).
Andya, et al., "The Effect of Formulation Excipients on Protein Stability and Aerosol Performance of Spray-Dried Powders of a Recombinant Humanized Anti-IgE Monoclonal Antibody", Pharm. Res., 1999, pp. 350-358, vol. 16, No. 3.
Anekwe, J., et al., "Relaxation Constants as a Predictor of Protein Stabilization", *Biocalorimetry: Applications of Calorimetry in the Biological Science*, J.E. Ladbury and B.Z. Chowdhry, editors, John Wiley & Sons, pp. 243-251 (1998).
Artursson, "Biodegradable microspheres V: Stimulation of macrophages with microparticles made of various poly saccharides", J. of Pharm. Sciences, p. 127-133.
Artursson, "Characterization of polyacryl starch microparticles as carriers for proteins and drugs", J. of Pharm. Sciences, p. 1507-1513.
Artursson, et al., "Receptor-mediated uptake of starch and mannan microparticles by macrophages relative contribution of receptors for complment immunoglobulins and carbohydrates", Biomaterials, 1988, pp. 241-246, vol. 9, No. 3.
Avrameas, et al., "Expression of a mannose/fucose membrane lectin on human dendritic cells", Eur. J. Immunol., 26:394-400, 1996.
Babincova et al. "Dextran Enhances Calcium-Induced Aggregation of Phosphatidylserine Liposomes: Possible Implications for Exocytosis" Physiol Res 48(4): 319-321 (1999).
Bach, J.F., "Insulin-dependent Diabetes Mellitus as an Autoimmune Disease", Endocr. Rev., 15 (4):516-542, 1994.
Baekkeskov, et al., "The Glutamate Decarboxylase and 38KD Autoantigens in Type 1 Diabetes: Aspects of Structure and Epitope Recognition", Autoimmunity, 15 Supp. 24-26, 1993.
Bandara, G., et al., "Interarticular Expression of Biologically Active Interleukin 1-Receptor-Antagonist Protein by Ex Vivo Gene Transfer", *Proc. Natl. Acad. Sci.*, 90:10764-10768 (Nov. 1993).
Barnett,.A.H., Exhubera Inhaled Insulin: A Review *Int. J. Clin. Pract* 58(4): 394-401 (2004).
Bell, J.H., et al., "Dry Powder Aerosols I: A New Powder Inhalation Device", J. Pharm. Sci., 60(10): 1559-1564 (Oct. 1971).
Belopol'skaya, T.V. et al. "The effect of water as natural plasticizer on thermal properties of denatured DNA studied by calorimetry" Vestnik Sankt-Peterburgskogo Universiteta Journal, Abstract Only, 1999, 2 pages.
Ben-Jebria, Abdellaziz et al., "Large Porous Particles for Sustained Protection from Carbochol-Induced Bronchoconstriction in Guinea Pigs," Pharm. Res., vol. 16 (No. 4), p. 555-561 (1999).
Bigsbee, et al. "Solid State Liability of Insulin: Comparison of Crystalline and Amorphous Forms", *Pharmaceutical Research* 10(10): Abstract No. PDD 7418, p. S-279 (1993).
Blakeley, et al., "Dry instant blood typing for bedside use", Lancet, 336: 854-855 (1990).
Block, et al., "Solubility and dissolution of triamcinolone acetonide", J. Pharm. Sci., 1973, 62(4), p. 617-621.

Bögelein, J., et al., "Influence of Amorphous Mannitol on Powder Properties of Spray Dried Trehalose/Dextran Mixtures", [on-line] [retrieved Sep. 2005] Retrieved from the Internet, 2 pages. (2003).
Bootsma, H.P.R., et al., "β-Cyclodestrin as an Excipient in Solid Oral Dosage Forms: In Vitro and In Vivo Evaluation of Spray-Dried Diazepan-β-Cyclodestrin Products", International Journal of Pharmaceutics 51:213-223 (1989).
Borgstrom et al., "Lung Deposition of Budesonide Inhaled via Turbuhaler," Eur. Respir. J, p. 69-73, (Feb. 26, 1994).
Bosquillon, C. et al., "Aerosolization Properties, Surface Composition and Physical State of Spray-Dried Protein Powders", *Journal of Controlled Release*, 99: 357-367 (2004).
Bot, "Receptor-mediated targeting of spray-dried lipid particles coformulated with immunoglobulin and loaded with a prototype vaccine", Pharm. Res., p. 971-979.
Branca, C., et al., "Destructuring effect of trehalose on the tetrahedral network of water: a Raman and neutron diffraction comparison", Physica A 304: 314-318 (2002).
Branchu, S., et al., "Hydroxypropyl-β-Cyclodextrin Inhibits Spray-Drying-Induced Inactivation of β- Galactosidase", *Journal of Pharmaceutical Sciences* 88(9): 905-911 (1999).
Branchu, S., et al., "The Effect of Cyclodestrins on Monomeric Protein Unfolding", *Biocalorimetry: Applications of Calorimetry in the Biological Sciences*, J.E. Ladbury and B.Z. Chowdhry (eds.), John Wiley & Sons, Ltd., 297-301 (1998).
Brange, et al., "Chemical Stability of Insulin, I, Hydrolytic Degradation During Storage of Pharmaceutical Preparations", *Pharmaceutical Research* 9(6): 715-726 (1992).
Breitenbach, J., "Melt Extrusion: From Process to Drug Delivery Technology", *European Journal of Pharmaceuticals and Biopharmaceutics* 54: 107-117 (2002).
Broadhead, et al. "The effect of process and formulation variable on the properties of spray-dried Beta-Galactosidase", Journal of Pharmaceutical Sciences 88(9): 905-911, 1999.
Broadhead, J., et al., *The Spray Drying of Pharmaceuticals*, 18 Drug Development and Industrial Pharmacy, p. 1169-1206 (1992).
Brown, "A Therapeutic Panorama of the Spongiform Encephalopathies", *Antiviral Chem. Chemother*. 1(2): 75-83 (1990).
Buckton et al. "The Use of Gravimetric Studies to Assess the Degree of Crystallinity of Predominantly Crystalline Powders" Int. J. of Pharmaceutics 123: 265-271 (1995).
Buitink, Julia, et al., *High Critical Temperature above Tg May Contribute to the Stability of Biological Systems*, 79 Biophysical Journal, 1119-1128 (Aug. 2000).
Buldt et al. "Neutron Diffraction Studies on Phosphatidylcholine Model Membranes" J. Mol. Biol. 134: 673-691 (1979).
Burvall, et al. "Storage of Lactose-Hydrolised Dried Milk: Effect of Water Activity on the Protein Nutritional Value", Journal of Dairy Research 45:381-389 (1978).
Bustami, et al., "Generation of Micro-Particles of Proteins for Aerosol Delivery Using High Pressure Modified Carbon Dioxide", Pharm. Res., 2000, pp. 1360-1366, vol. 17, No. 11.
Byron, Peter R., et al., Drug Carrier Selection—Important Physicochemical Characteristics Respiratory Drug Delivery, 5th Ed., Interpharm Press., 103-113 (1996).
Byström et al., "Microcalorimetry—A Novel Technique for Characterization of Powders", *Respiratory Drug Delivery IV*, p. 297-302 (1994).
Carpenter, John F., et al., "Rational Design of Stable Lyophilized Protein Formulations: Some Practical Advice", *Pharmaceutical Res.*, 14(8): 969-975 (1997).
Casselyn, M. et al., *Time-Resolved Scattering Investigations of Brome Mosaic Virus Microcrystals Appearance* D58 Acth Cryst. 1568-1570 (2002).
Caughey, et al., "Sulphated Polyanion Inhibition of Scrapie-Associated PrP Accumulation in Cultured Cells", *J. Virol*., 67(2): 643-650 (1993).
Cevc. G. "Membrane Electrostatics" Biochim Biophys Acta 1031(3): 311-382 (1990)., in particular pp. 330-338.
Chan, et al., "Formulation of Vaccine Ajuvant Muramyldipeptides (MDP). 1 Characterization of Amorphous and Crystalline Forms of a Muramyldipeptide analogue", Pharmaceutical Research, 5(8): 523-527 (1988).

Chan, Hak-Kim, et al., "Physical Stability of Salmon Calcitonin Spray-Dried Powders for Inhalation", *Journal of Pharmaceutical Sciences*, 93(3): 792-804 (2004).
Chan, Hak-Kim, et al., "Solid State Characterization of Spray-Dried Powders of Recombinant Human Deoxyribonuclease (RhDNase)", *Journal of Pharmaceutical Sciences*, 87(5): 647-654 (1998).
Chavan, V., et al., "Effect of Rise in Simulated Inspiratory Flow Rate and Carrier Particle Size on Poweder Emptying From Dry Powder Inhalers", *AAPS Pharsci* 2000; 2(2) article 10 [on-line] Retrieved from the Internet 7 pages (2000).
Chavan, V., et al., "Novel System to Investigate the Effects of Inhaled Volume and Rates of Rise in Simulated Inspiratory Air Flow on Fine Particle Output From a Dry Power Inhaler", *AAPS Pharmisci* 2002; 4(2) article 6, pp. 1-6.
Chavan, V., et al., Effect of Particle Size and Rise in Simulated Inspiratory Flow Rate on Device Emptying in a Dry Powder Inhaler SYstem, [on-line] [retrieved Jan. 7, 2005] Retrieved from the Internet 1 page (1999).
Chawla, et al., "Production of Spray Dried Salbutamol Suplhate for Use in Dry Powder Aerosol Formulation", *International Journal of Pharmaceutics*, 108: 233-240 (1994).
Chiou, et al., "Pharmaceutical Applications of Solid Dispersion Systems", J. Pharm., 60(9): 1281-1302 (1971).
Christensen, et al., "Preparation of Redispersible Dry Emulsions by Spray Drying", Int. J. of Pharm., 2001, pp. 187-194.
Cicogna et al., "Efficacy of prophylactic aerosol amphotericin B lipid complex in a rat model of pulmonary aspergillosis", Antimicrobial Agents and Chemotherapy, 1997, 41 (2), p. 259-261.
Cleland, et al., "The Development of Stable Protein Formulations: A Close Look at Protein Aggregation, Deamidation and Oxidation", *Critical Reviews in Therapeutic Drug Carrier Systems*, 10(4): 307-377 (1993).
Cline D., "Predicting the Quality of Powders for Inhalation from Surface Energy and Area", *Pharmaceutical Research*, 19(9): 1274-1277 (2002).
Cline, D., et al., "Predicting the Quality of Powders for Inhalation", *Respiratory Drug Delivery VIII*p. 683-685 (2002).
Colaco, et al., "Chapter 14: Chemistry of Protein Stabilization by Trehalose", ACS *Symposium Series 567, Formulation and Delivery of Proteins and Peptides*, J.L. Cleland & R. Langer, pp. 222-240 (1994).
Colaco, et al., "Extraordinary Stability of Enzymes Dreid in Trehalose: Simplified Molecular Biology", *Bio/Technology* 10: 1007-1011 (1992).
Colaco, et al., "Trehalose Stabilization of Biological Molecules", *Biotechnol. Internet*., pp. 345, 347-350 (1992).
Considine, G.D., et al., *Van Nostrand's Scientific Encyclopedia*, 9th edition, vol. 2, Wiley-Interscience, John Wiley & Sons, Inc., Definition of Vaccines: pp. 3591-3592 (2002).
Constantino, et al., "Moisture-Induced Aggregation of Lyophilized Insulin", *Pharmaceutical Research*, 11(1): 21-29 (1994).
Constantino, H.R., et al., "Effect of Mannitol Crystallization on the Stability and Aerosol Performance of a Spray-Dried Pharmaceutical Protein, Recombinant Humanized Anti-IgE Monoclonal Antibody", *Journal of Pharmaceutical Sciences*, 87(11): 1406-1411 (1998).
Controlled Release Society, Inc.
Cox, "Adjuvants—a classification and review of their modes of action", Vaccine, p. 248-256.
Craig, I.D., et al., "Mailiard Reaction Kinetics in Model Preservation Systems in the Vicinity of the Glass Transition: Experiment and Theory", *J. Agric. Food Chem*. 49(10: 4706-4712 (2001).
Crommelin, et al., "Liposomes", Chapter 3, *Colloidal Drug Delivery Systems*, J. Kreuter, editor: 73-190 (1994).
Crowe, et al., "Are Freezing and Dehydration Similar Stress Vectors? A Comparison of Modes of Interaction of Stabilizing Solutes with Biomolecules", Cryobiol. 27: 219-231 (1990).
Crowe, et al., "Interations of Sugars with Membranes", Biochimica et Biophysica Acta, 947: 367-384 (1988).
Crowe, John H., et al., "The Role of Vitrification in Anhydrobiosis", *Annu. Rev. Physiol*., 60: 73-103 (1998).
Crowe, Lois M., et al., "Is Trehalose Special for Preserving Dry Biomaterials?", *Biophysical Journal*, 71: 2087-2093 (1996).

Daemen, et al., "The Destruction of Enzymes and Bacteria During the Spray-Drying of Milk and Whey, 2. the Effect of the Drying Conditions", Neth. Milk Dairy J., 36: 211-229 (1982).
Dahl, et al., "Selective induction of transforming growth factor beta in human monocytes by lipoarabinomannan of *Mycobacterium tuberculosis*", Infection and Immunity, 64:399-405, 1996.
Dalby, et al., "Relationship Between Particles Morphology and Drug Release Properties After Hydration of Aerosols Properties Containing Liposome Forming Ingredients", *Pharmaceutical Research*, 5(10): S-94, Abstract PD 888 (1988).
Dalby, R.N., et al., "Droplets Drying and Electrostatic Collection a Novel Alternative to Conventional Comminution Techniques", *Journal of Biopharmaceutical Sciences* 3 (1/2): 091-099 (1992).
Dalby, R.N., et al., "Inhalation Therapy: Technological Milestones in Asthma Treatment", *Advanced Drug Delivery*, 55: 779-791 (2003).
Daniel, et al., "Epitope specificity, cytokine production profile and diabetogenic activity of insulin-specific T cell clones isolated from NOD mice", Eur. J. Immunol., 25:1056-1062, 1995.
Darrington, et al., "Evidence for a Common Intermediate in Insulin Deamidation and Covalent Dimer Formation: Effects of pH and Aniline Trapping in Dilute Acidic Solutions", *Journal of Pharmaceuticals Sciences*, 84(3): 275-282 (1995).
D'Cruz, N. "Relationship Between Protein Thermal Stability and Glass Transition in Gelatin Polyol and Gelatin-Water Mixtures", Proceedings of 2004 Meeting IFT, Jul. 12-16, 2004, Las Vegas, NV, Session 17E, Food Chemistry: Proteins, [on-line].
Decarlo, S., et al., "Unexpected Property of Trehakose as Observed by Cyro-Electron Microscopy", *Journal of icroscopy*, 196(1): 40-45 (1995).
Dellamary et al. "Hollow Porous Particles in Metered Dose Inhalers" Pharm Research 17(2): 168-174 (2000).
DeYoung, "The AeroDose Multidose Inhaler Device Design and Delivery Characteristics", *Respiratory Drug Delivery VI*, p. 91 (1998).
D'Hondt, "Possible Approaches to Develop Vaccines Against Hepatitis A", Vaccine 10 (Supplement 1): S48-S52 (1992).
Dose, et al., "Survival in Extreme Dryness and DNA-Single-Strand Breaks", *Advances in Space Research*, 12(4)221-229 (1992).
Dunbar et al., "Dispersion and Characterization of Pharmaceutical Dry Powder Aerosols," KONA (Feb. 26, 1998).
During, M.J., et al., "Long-Term Behavioral Recovery in Parkinsonian Rats by an HSV Vector Expressing Tyrosine Hydrosylase", *Science*, 266(5189): 856-857 (Nov. 1994).
Duzgunes et al. "Studies on the Mechanism of Membrane Fusion. Role of Head-Group Composition in Calcium- and Magnesium-induced Fusion of Mixed Phospholipid Vesticles" Biochim Biophys Acta 642: 182-195 (1981).
Ebara et al. "interactions of Calcium Ions with phospholipid Membranes" Langmuir 10: 2267-2271 (Apr. 1994).
Edwards, A.D., et al., "Crystallization of Pure Anhydrous Polymorphs of Carbamazepine by Solution Enhanced Dispersion with Supercritial Fluids (SEDS™)", *Journal of Pharmaceutical Sciences*, 90(8): 1115-1124 (2001).
Edwards, et al., "Large Porous Particles for Pulmonary Drug Delivery", *Science*, vol. 276, pp. 1868-1871 (Jun. 1997).
Eisenberg et al. "Adsorption of Monovalent Cations to Bilayer Membranes Containing Negative Phospholipids" Biochemistry 18(23):5213-5223 (1979).
Eleutherio, et al., "Role of the Trehalose Carrier in Dehydration Resistence of *Saccharomyces cerevisiae", Biochimica et Biophysica Acta*, 1156: 263-266 (1993).
Elkordy, et al., Integrity of Crystalline Lysozyme Exceeds that of a Spray-Dried Form, *International Journal of Pharmaceutics*, 247: 79-90 (2002).
Evora, "Relating the phagocytosis of microparticles by alveolar macrophages to surface chemistry: the effect of 1,2-dipalmitoylphosphatidylcholine", J. of Cont. Rel., p. 143-152.
Office Action in U.S. Appl. No. 10/644,265 (patented as 7,628,978) dated Feb. 1, 2007.
Office Action in U.S. Appl. No. 10/644,265 (patented as 7,628,978) dated Mar. 20, 2008.
Office Action in U.S. Appl. No. 10/644,265 (patented as 7,628,978) dated May 9, 2006.
Office Action in U.S. Appl. No. 10/644,265 (patented as 7,628,978) dated Oct. 7, 2005.
Office Action in U.S. Appl. No. 12/012,827 dated Oct. 21, 2009.
Office Action in U.S. Appl. No. 10/616,448 dated Feb. 25, 2010.
Office Action in U.S. Appl. No. 10/616,448 dated Apr. 16, 2008.
Office Action in U.S. Appl. No. 10/616,448 dated May 4, 2006.
Office Action in U.S. Appl. No. 10/616,448 dated Aug. 19, 2005.
Office Action in U.S. Appl. No. 10/616,448 dated Sep. 25, 2009.
Office Action in U.S. Appl. No. 10/616,448 dated Oct. 25, 2004.
Office Action in U.S. Appl. No. 10/616,448 dated Nov. 14, 2008.
Office Action in U.S. Appl. No. 09/218,212 (patented as 6,309,623) dated May 17, 1999.
Office Action in U.S. Appl. No. 09/218,212 (patented as 6,309,623) dated Jul. 28, 2000.
Office Action in U.S. Appl. No. 09/218,212 (patented as 6,309,623) dated Dec. 20, 2000.
Office Action in U.S. Appl. No. 11/187,757 dated Mar. 26, 2010.
Office Action in U.S. Appl. No. 09/219,736 (patented as 6,565,885) dated Aug. 29, 2001.
Office Action in U.S. Appl. No. 09/219,736 (patented as 6,565,885) dated Dec. 20, 2000.
Office Action in U.S. Appl. No. 09/219,736 (patented as 6,565,885) dated Jun. 29, 1999.
Office Action in U.S. Appl. 09/862,764 (patented as 6,638,495) dated Nov. 1, 2002.
Office Action in U.S. Appl. No. 10/096,780 (patented as 7,306,787) dated Jan. 25, 2006.
Office Action in U.S. Appl. No. 10/096,780 (patented as 7,306,787) dated Apr. 19, 2005.
Office Action in U.S. Appl. No. 10/096,780 (patented as 7,306,787) dated May 20, 2003.
Office Action in U.S. Appl. No. 10/096,780 (patented as 7,306,787) dated Jun. 17, 2004.
Office Action in U.S. Appl. No. 10/096,780 (patented as 7,306,787) dated Oct. 2, 2002.
Office Action in U.S. Appl. No. 10/132,215 (patented as 7,141,236) dated Nov. 3, 2005.
Office Action in U.S. Appl. No. 10/327,510 (patented as 7,368,102) dated Jan. 14, 2007.
Office Action in U.S. Appl. No. 10/327,510 (patented as 7,368,102) dated May 4, 2006.
Office Action in U.S. Appl. No. 10/327,510 (patented as 7,368,102) dated Jun. 28, 2005.
Office Action in U.S. Appl. No. 10/327,510 (patented as 7,368,102) dated Sep. 20, 2004.
Office Action in U.S. Appl. No. 09/568,818 dated Jan. 24, 2006.
Office Action in U.S. Appl. No. 09/568,818 dated Feb. 26, 2008.
Office Action in U.S. Appl. No. 09/568,818 dated Apr. 7, 2005.
Office Action in U.S. Appl. No. 09/568,818 dated Apr. 10, 2002.
Office Action in U.S. Appl. No. 09/568,818 dated May 5, 2004.
Office Action in U.S. Appl. No. 09/568,818 dated Jun. 4, 2007.
Office Action in U.S. Appl. No. 09/568,818 dated Jul. 29, 2003.
Office Action in U.S. Appl. No. 09/568,818 dated Oct. 6, 2006.
Office Action in U.S. Appl. No. 09/568,818 dated Nov. 5, 2002.
Office Action in U.S. Appl. No. 09/568,818 dated Dec. 8, 2008.
Office Action in U.S. Appl. No. 09/851,226 (patented as 7,442,388) dated Feb. 11, 2003.
Office Action in U.S. Appl. No. 09/851,226 (patented as 7,442,388) dated Mar. 22, 2005.
Office Action in U.S. Appl. No. 09/851,226 (patented as 7,442,388) dated May 5, 2004.
Office Action in U.S. Appl. No. 09/851,226 (patented as 7,442,388) dated Jun. 24, 2002.
Office Action in U.S. Appl. No. 09/851,226 (patented as 7,442,388) dated Jul. 24, 2003.
Office Action in U.S. Appl. No. 09/851,226 (patented as 7,442,388) dated Dec. 21, 2005.
Office Action in U.S. Appl. No. 10/141,219 dated Jan. 8, 2009.
Office Action in U.S. Appl. No. 10/141,219 dated Mar. 10, 2006.
Office Action in U.S. Appl. No. 10/141,219 dated Mar. 26, 2010.
Office Action in U.S. Appl. No. 10/141,219 dated Jun. 6, 2005.
Office Action in U.S. Appl. No. 10/141,219 dated Jul. 21, 2008.
Office Action in U.S. Appl. No. 10/141,219 dated Aug. 18, 2009.

Office Action in U.S. Appl. No. 10/141,219 dated Oct. 23, 2003.
Office Action in U.S. Appl. No. 10/141,219 dated Nov. 15, 2004.
Office Action in U.S. Appl. No. 10/141,219 dated Nov. 29, 2006.
Office Action in U.S. Appl. No. 12/258,163 dated Sep. 28, 2009.
Office Action in U.S. Appl. No. 10/612,393 dated Feb. 9, 2006.
Office Action in U.S. Appl. No. 10/612,393 dated May 4, 2005.
Office Action in U.S. Appl. No. 10/612,393 dated Aug. 1, 2006.
Office Action in U.S. Appl. No. 10/612,393 dated Aug. 10, 2005.
Office Action in U.S. Appl. No. 11/317,523 dated Apr. 10, 2009.
Office Action in U.S. Appl. No. 11/317,523 dated Sep. 25, 2008.
Office Action in U.S. Appl. No. 11/317,523 dated Oct. 1, 2009.
Office Action in U.S. Appl. No. 11/317,839 dated Apr. 13, 2009.
Office Action in U.S. Appl. No. 11/317,839 dated Sep. 25, 2008.
Office Action in U.S. Appl. No. 11/317,839 dated Dec. 23, 2009.
Office Action in U.S. Appl. No. 09/919,477 dated Feb. 11, 2004.
Office Action in U.S. Appl. No. 10/916,246 dated Mar. 19, 2009.
Office Action in U.S. Appl. No. 10/916,246 dated Mar. 25, 2008.
Office Action in U.S. Appl. No. 10/916,246 dated Jun. 19, 2007.
Office Action in U.S. Appl. No. 10/916,246 dated Oct. 28, 2009.
Office Action in U.S. Appl. No. 09/888,311 dated Jan. 8, 2003.
Office Action in U.S. Appl. No. 09/888,311 dated Jun. 25, 2002.
Office Action in U.S. Appl. No. 09/888,311 dated Dec. 5, 2001.
Office Action in U.S. Appl. No. 09/218,209 (patented as 6,433,040) dated Jan. 29, 2001.
Office Action in U.S. Appl. No. 09/218,209 (patented as 6,433,040) dated Feb. 15, 2000.
Office Action in U.S. Appl. No. 09/218,209 (patented as 6,433,040) dated May 26, 1999.
Office Action in U.S. Appl. No. 09/999,071 (patented as 7,205,343) dated Jan. 18, 2006.
Office Action in U.S. Appl. No. 09/999,071 (patented as 7,205,343) dated Jan. 23, 2004.
Office Action in U.S. Appl. No. 09/999,071 (patented as 7,205,343) dated Jun. 17, 2003.
Office Action in U.S. Appl. No. 09/999,071 (patented as 7,205,343) dated Aug. 12, 2005.
Office Action in U.S. Appl. No. 09/999,071 (patented as 7,205,343) dated Oct. 7, 2004.
Office Action in U.S. Appl. No. 11/675,073 (patented as 7,393,544) dated Sep. 17, 2007.
Office Action in U.S. Appl. No. 09/218,213 (patented as 6,946,117) dated Apr. 28, 2000.
Office Action in U.S. Appl. No. 09/218,213 (patented as 6,946,117) dated May 19, 2004.
Office Action in U.S. Appl. No. 09/218,213 (patented as 6,946,117) dated Jun. 29, 1999.
Office Action in U.S. Appl. No. 09/218,213 (patented as 6,946,117) dated Nov. 16, 2000.
Office Action in U.S. Appl. No. 09/720,536 (patented as 6,630,169) dated Jul. 15, 2002.
Office Action in U.S. Appl. No. 11/076,430 dated Mar. 3, 2010.
Office Action in U.S. Appl. No. 11/076,430 dated May 11, 2009.
Office Action in U.S. Appl. No. 11/076,430 dated Nov. 13, 2008.
Office Action in U.S. Appl. No. 10/141,032 dated May 20, 2005.
Office Action in U.S. Appl. No. 10/141,032 dated Jul. 16, 2003.
Office Action in U.S. Appl. No. 10/141,032 dated Aug. 17, 2004.
Office Action in U.S. Appl. No. 10/141,032 dated Oct. 23, 2002.
Office Action in U.S. Appl. No. 09/886,296 dated Mar. 28, 2007.
Office Action in U.S. Appl. No. 09/886,296 dated Apr. 16, 2004.
Office Action in U.S. Appl. No. 09/886,296 dated Apr. 22, 2008.
Office Action in U.S. Appl. No. 09/886,296 dated Jun. 6, 2006.
Office Action in U.S. Appl. No. 09/886,296 dated Jun. 19, 2002.
Office Action in U.S. Appl. No. 09/886,296 dated Jun. 22, 2009.
Office Action in U.S. Appl. No. 09/886,296 dated Jul. 21, 2003.
Office Action in U.S. Appl. No. 09/886,296 dated Nov. 2, 2005.
Office Action in U.S. Appl. No. 09/886,296 dated Nov. 9, 2007.
Office Action in U.S. Appl. No. 09/886,296 dated Dec. 5, 2008.
Office Action in U.S. Appl. No. 09/886,296 dated Dec. 11, 2002.
Fahy, et al., "Vitrification as an Approach to Cryopreservation", Cryobiology, 21: 407-426 (1984).
Fakes, M., et al., "Moisture Sorption Behavior of Selected Bulking Agents Used in Lyophilized Products", PDA J. Pharm. Sci. Technol. 54(2) 144-149, Abstract only [on-line] [retrieved Sep. 25, 2005] Retrieved from the Internet (2002).
Finar, I.L., "§14. Trehalose, m.p. 203°C", under "Carbohydrate" Organic Chemistry, vol. 2, Stereochemistry and the Chemistry of Natural Products, 5th edition, Longman, p. 323 (1996).
Forbes, R.T., et al., "Water Vapor Sorption Studies on the Physical Stability of a Series of Spray-Dried Protein/Sugar Powders for Inhalation", Journal of Pharmaceutical Sciences, 87(11): 1316-1321 (1998).
Franks, "Accelerated Stability Testing of Bioproducts: Attractions and Pitfalls", Tibtech, 12: 114-117 (1994).
Franks, "Freeze Drying: From Empiricism to Predictability", Cyro-Letters, 11: 93-110 (1990).
Franks, "Materials Science and the Production of Shelf-Stable Biologicals", Pharmaceutical Technology International, 24: 24-34 (Oct. 1991).
Franks, "Separation, Improved Freeze-Drying, an Analysis of the Basic Scientific Principles", Process Biochemistry, 24(1): iii-vii (1989).
French, Donna L., et al., "The Influence of Formulation on Emission, Deaggregation and Deposition of Dry Powders for Inhalation," J. Aerosol Science, vol. 27, No. 5, pp. 769-783 (1996).
Fukuoka, et al., "Glassy State of Pharmaceuticals. V. Relaxation During Cooling and Heating of Glass by Differential Scanning Calorimetry", Chem. Pharm. Bull 39(8): 2087-2090 (Aug. 1991).
Garner, et al., "Secretion of TNF-{alpha} by alveolar macrophages in response to Candida albicans mannan", J. Leukoc. Biol., 55:161-168, 1994.
Goldbach et al. "Spray-Drying of Liposomes for a Pulmonary Administration I. Chemical Stability of Phospholipids" Drug Develop Ind Pharm 19(19): 2611-2622 (1993).
Gonda, et al., "Characterization of Hygroscopic Inhalation Aerosols", in: Particle Size Analysis, (Eds. N.G. Stanley-Wood and T. Allen, Wiley Heyden Ltd., NY), pp. 31-43 (1981).
Gordon et al. "Ideal Copolymers and the Second-Order Transitions of Synthetic Rubbers. I. Non-Crystalline Copolymers" J. Appl. Chem. 2: 493-500 (Sep. 1952).
Gower's Handbook of Industrial Surfactants 2993, pp. 885-904.
Green, et al., "Phase Relations and Vitrification in Saccharide-Water Solutions and the Trehalose Anomaly", J. Phys. Chem., 98: 2880-2882 (1989).
Green, et al., "The Protein-Glass Analogy: Some Insights from Homopeptide Comparisons", J. Phys. Chem., 98: 13780-13790 (Apr. 1994).
Gupta, A., et al., "Single Virus Particle Mass Detection Using Microresonators with Nanoscale Thickness", Applied Physics Letters, 84(11): 1976-1978 (2004).
Hahn, et al., "Solid Surfactant Solutions of Active Ingredients in Sugar Esters", Pharmaceutical Research, 6: 958-959 (1989).
Haitsma, et al., "Exogenous Surfactant as a Drug Delivery Agent", Adv. Drug Del. Rev., 2001, pp. 197-207.
Hancock et al. "Characteristics and Significance of the Amorphous State in Pharmaceutical Systems" J. of Pharmaceutical Sciences 86(1): 1-12 (Jan. 1997).
Hancock et al. "The Relationship Between the Glass Transition Temperature and the Water Content of Amorphous Pharmaceutical Solids" Pharm Research 11(4):471-477 (1994).
Hancock, B.C., et al., "The Effect of Temperature on Water Vapor Sorption by Some Amorphous Pharmaceutical Sugars", Pharmaceutical Development and Technology, 4(1): 125-131 (1999).
Hancock, et al., "The Use of Solution Theories for Predicting Water Vapor Absorbtion by Amorphous Pharmaceutical Solids: A Test of the Flory-Huggins and Vrentas Models", Pharmaceutical Research, 10(9): 1262-1267 (1993).
Hancock, et al., "A Pragmatic Test of Simple Calorimetric Method for Determining the Fragility of some Amorphous Pharmaceutical Materials", Pharm. Res., 15(5): 762-767 (1998).
Hancock, et al., "Molecular Mobility of Amorphous Pharmaceutical Solids Below Their Glass Transition Temperatures", Pharmaceutical Research, 12(6): 799-806 (1995).
Hanes, et al., "Porous Dry-Powder PLGA Microspheres coated with Lung Surfactant for Systematic Insulin Delivery via the Lung", Proc. Int'l. Symp. Control Rel. Bioactive Matter, 24:57-58 (1997).

Hanes, Justin, "Polymer Microspheres for Vaccine Delivery", Thesis (Ph.D.), dated Sep. 1996, archived by MIT library Jul. 31, 1997 and catalogued on Dec. 5, 1997.
Harwood, C.F., "Compact Effect on Flow Property Indexes for Powders", *J. Pharm. Sci* 60:161-163 (1971).
Hatley, R.H.M., et al., "Stabilization of Labile Materials by Amorphous Carbohydrates Glass Fragility and the Physiochemical Properties that make Trehalose a Superior Excipient", *Pharmaceutical Research*, 13(9 Suppl.) PDD 7165: S274 (1996).
Hauser et al. "Comparative Structural Aspects of Cation Binding to Phosphatidylserine Bilayers" Biochim Biophys Acta 813: 343-346 (1985).
Hauser et al. "Interactions of Divalent Cations with Phosphatidylserine Bilayer Membranes" Biochemistry 23: 34-41 (1984).
Heitefuss, R., et al., "The Stabilization of Extracts of Cabbage Leaf Proteins by Polyhydroxy Compounds for Electrophoretic and Immunological Studies", Archives of Biochemistry and Biophysics, 85: 200-208 (1959).
Heller, Martin C., et al., *Protein Formulation and Lyophilization Cycle Design: Prevention of Damage Due to Freeze-Concentration Induced Phase Separation* 63 Biotechnology & Bioengineeting, 166-174 (1999).
Herrington, T.M., et al., "Physico-Chemical Studies on Sugar Glasses. I. Rates of Crystallization", Journal of Food Technology, 19: 409-425 (1984).
Hickey, A. J. et al., "Behavoir of Hygroscopic Pharmaceutical Aerosols and the Influence of Hydrophobic Additives," *Pharmaceutical Research* 10(1):1-7 (1993).
Hickey, A. J. et al., "Methods of Aerosol Particle Size Charaterization," *Pharmaceutical Inhalation Aerosol Technology* 8:219-253 (1992).
Hoener, Betty-Ann et al., "Factors Influencing Drug Absorption and Availability" *Modern Pharmaceutics*, Gilber S. Banker et al., eds., Marcel Dekker Inc., Chapter 4, pp. 121-153 (1996).
Hrkach et al., "Poly-lactic-co-amino acid) graft copolymers: A class of . . . polymers for bioaplication," Hydrogels and Biodegradable Polymers for Bioapplication (1996), ACS Symposium Series No. 627, pp. 93-101.
Hrkach et al., "Synthese of polylactic acid-co-lysine graft copolymers," Macromolecules 1995, 28(13):4736-4739.
Huster et al. "Investigation of Phospholipid Area Compression Induced by Calcium-Mediated Dextran Sulfate Interaction" Biophys J. 77(2): 879-867 (Aug. 1999).
Huster et al. "Strength of Ca(2+) Binding to Retinal Lipid Membranes: Consequences for Lipid Organization" Biophys J. 78(6): 3011-3018 (Jun. 2000).
Ibrahim, A. L. et al., "Sprah Vaccination With an Improved F Newcastle Disease Vaccine. A Comparison of Efficacy With the B1 and La Sota Vaccines," Br. Vet. J. 139:213-219 (1983).
Igaki, N. et al., "The Inhibition of the Maillard Reaction by L Lysine In-Vitro," *J. Jpn. Diabetes Soc.*, english abstract 34(5):403-407 (1991).
Iglesias et al., "Adsorption Isotherm of Amorphous Trehalos", *J. Sci. food Agric.* 75:183-186 (1997).
International Search Report, PCT/US01/24038, issued Jul. 17, 2002.
International Search Report, PCT/US02/13145, dated Aug. 20, 2002.
Jacobson et al. "Phase Transition and Phase Separations in Phospholipid Membranes Induced by Changes in Temperature, pH, and Concentration of Bivalent Cations" 14(1): 152-161 (1975).
Jameel, F. et al., "Freeze Drying Properties of Some Oligonucleotides", *Pharmaceutical Development and Technolology* 6(2):151-157 (2001).
Jeffery, "The preparation and characterization of poly(lactide-co-clycolide) microparticles. II. The entrapment of a model proein using a (water-in-oil)-in-water emulsion solvent evaporation technique", Pharm. Res., p. 362-368.
JM. Goldman et al., "Inhaled Micronised Gentamicin Powder: A New Delivery System," Thorax, BMJ Publishing Group, GB, vol. 45, No. 12, Dec. 1990, p. 939-940 XP001057935.
Johansen, et al., "Technological Considerations Related to the Up-Scaling of Protein Microencapsulation by Spray-Drying", Eur. J. of Pharm. And Biopharm., 2000, pp. 413-417.

Johnson, Preparation of peptide and protein powders for inhalation, Advanced Drug Delivery Reviews 26 (1997) 3-15.
Jovanovic-Peterson, L. et al., "Jet-injected insulin is associated with decreased antibody production and postprandial glucose variability when compared with needle injected insulin in gestational diabetic women," Diabetes Care 16(11):1479-1484 (Nov. 1993).
Kachura, "Method of Drying Lactic Acid Bacteria," Vinodelie I Vinogradarstvo SSSR 2:49-50, English Abstract only, one page (1985).
Kanna, K. et al., "Denaturation of Fish Muscle Protein by Dehydration" *Bull Tokai Reg. Fish. Res. Lab.* 77:70-76 English abstract (1974).
Karmas. R, et al., "Effect of Glass Transition on Rates of Nonenzymatic Browning in Food Systems," *J. Agric. Food Chem.* 40:873-879 (1992).
Keller, et al., "Insulin prophylaxis in individuals at high risk of type I diabetes", Lancet, 341:927-928, 1993.
Khan, R. "Chemistry and New Uses of Sucrose: How Important?" Pure & Appl. Chem. 56(7):833-844 (1984).
Khan, R. "Cyclic Acetals of 4,1', 6-Tricholoro-4,1', 6-Trideoxy-Galacto-Sucrose and Their Conversion Into Methyl Ether Derivatives," Carb. Res. 198:275-283 (1990).
Kimpimaki, et al., "Disease-Associated Autoantibodies as Surrogate Markers of Type 1 Diabetes in Young Children at Increased Genetic Risk", J. clin. endocrinol. Metab., 85:1126-1132, 2000.
Klein, T. M. et al., "High Velocity Microprojectiles for Delivering Nucleic Acids Into Living Cells," Nature 327:70-73 (1987).
Kwon et al. "Calcium Ion Adsorption on Phospholipid Bilayers—Theoretical Interpretation" J Jap Oil Chem Soc 43(1):23-30 (1994).
Labrude, P. et al., "Protective Effectof Sucrose on Spray Drying of Ocxyhemoglobin," Journal of Pharmaceutical Sciences. 78(3):223-229 (1989).
Labuza el al., "Glass Transition Temperatures of Food Systems", [on-line] [retrieved Sep. 2005] Retrieved from the Internet pp. 1-31 (Jan. 1992).
Lai, M. C. et al., "Solid-State Chemical Stability of Proteins and Peptides", *Journal of Pharmaceutical Sciences* 88(5):489-500 (1999).
Laube, B. L. et al., "Targeting Aerosol Deposition in Patients With Cystic Fibrosis, Effects of Alterations in Particle Size and Inspiratory Flow Rate", Chest 118(4): 1069-1076 (2000).
Ledt, F., et al., "New Aspects of the Maillard Reaction in Foods and in the Human Body," Ang. Chem. Int. Ed. Engl. 29:565-594 (Jun. 1990).
Lee, C. K. *Developments in Food Carbohydrate*—2nd edition Applied Science Publishers, London, Table of Contents, 4 pages (1980).
Lee, G., "Spray Drying of Proteins," Chapter 6, *Rational Design of Stable Protein Formulations, Theory and Practice*, J. F. Carpenter & M. Manning, pp. 135-158 (2002).
Lehninger, Albert L. *The Molecular Basis of Cell Structure and Function* Biochemistry, Chapter 31, 859-890 (Worth Publishers Inc., 2nd edition, 1975).
Leslie, S. B. et al., "Trehalose and sucrose protect both membranes and proteins in intact bacteria during drying", *Appl. Env. Microbiol.* 61(10): 3592-3597 (1995).
Leuner, C. et al., "Improving Drug Solubility for Oral Delivery Using Solid Dispersions", European Journal of Pharmaceutics and Biopharmaceutics 50:47-60 (2000).
Levine et al., "Another View of Trehalose for Drying and Stabilizing Biological Materials," Biopharm 5:36-40 (1992).
Li, Z. et al., "Realistic In Vitro Assessment of Dry Powder Inhalers", *Respiratory Drug Delivery VIII*, pp. 687-689 (2002).
Lin, S.-Y. et al., "Solid Particles of Drug-β-Cyclodextrin Inclusion Complexes Directly Prepared by a Spray-Drying Technique", International Journal of Pharmaceutics, 56:249-259 (1989).
Lis et al. "Adsorption of Divalent Cations to a Variety of Phosphatidylcholine Bilayers" Biochemistry 20: 1771-1777 (1981).
Lis et al. "Binding of Divalent Cations to Dipalmitoylphosphatidytcholine Bilayers and its Effect on Bilayer Interaction" Biochemistry 20: 1761-1770 (1981).

Liu, Jinsong et al., "Dynamics of Pharmaceutical Amorphous Solids: The Study of Enthalpy Relaxation by Isothermal Microcalorimetry", *Journal of Pharmaceutical Sciences* 91(8):1853-1862 (2002).

Louey, M. D. et al., "Controlled Release Products for Respiratory Delivery", *APR*, 7(4):82-87 [on-line] retreived 09/20051 <http://www.americanpharmaceuticalreview.com.article.aspx?article=77 (2004).

Louis, P. et al., "Survival of *Escherichia coli* During Drying and Storage in the Presence of Compatible Solutes" *Appl. Microbiol. Biotechnol*. 41:684-688 (1994).

Lueckel, B. et al., "Effects of Formulation and Process Variables on the Aggregation of Freeze-Dried Interleukin-6 (IL-6) After Lyophilization and on Storage", *Pharmaceutical Development and Technology* 3(3):337-346 (1998).

MacKenzie, "Collapse During Freeze Drying-Qualitative and Quantitative Aspects." *Freeze Drying and Advanced Food Technology*, edited by Goldblith, Rey and Rothmayr: 277-307 (1975).

Makower, B. et al., "Equilibrium Moisture Content and Crystallization of Amorphous Sucrose and Glucose," Agric. And Food Chem. 4(1):72-77 (1956).

Martin, A. et al., States of Matter and Phase Equilibria Physical Pharmacy, Physical Chemical Principles in the Pharmaceutical Sciences, 3rd. ed., Chapter 4, 62-92 (1983).

Masinde, Lwandiko E., et al., "Aerosolized Aqueous Suspension of Poly(L-lactic Acid) Microspheres,", 100 *International Journal of Pharmaceutics*, pp. 123-131 (1993).

Masters, K Spray Drying Handbook, 5th ed., Chapters 13 and 15, pp. 491-537 and 587-642 (1991).

Masters, K. Spray Drying Handbook, England; Longman Scientific & Technical and John Wiley & Sons, Inc., 5th ed. Chapter 8, pp. 309-352 (1991).

Masters, K. Spray Drying Handbook, England; Longman Scientific & Technical, 5th ed., pp. 640-842 (1991).

Matsuda, Y. et al., "Amorphism and Physicochemical Stability of Spray Dried Frusemide," *J. Pharm,. Pharmacol*. 44:627-633, received Nov. 7, 1991 (1992).

Mattern et al., "Formulation of Proteins in Vacuum-Dried Glasses. II. Process and Storage Stability in Sugar-Free Amino Acid Systems", Pharmaceutical Development & Technology 4(2):199-208 (1999).

Merck Index 11 ed., p. 313, 1989.

Miller, D. P. et al., "Stabilization of Lactate Dehydrogenase Following Freeze Thawing and Vacuum-Drying in the Presence of Trehalose and Borate", *Pharmaceutical Research* 15(8):1215-1221 (1998). (7 pages) Cited by 7 patents [ISI abstract].

Millqvist-Fureby et al. "Spray-Drying of Trypsin—Surface Characterisation and Activity Preservation" Int. J. Pharm. 188: 243-253 (1999).

Millqvist-Fureby et al. "Surface Characterisation of Freeze-Dried Protein/Carbohydrate Mixtures" Int. J. Pharm. 191: 103-114 (1999).

Mitra et al, Enhanced Pulmonary Delivery of Insulin by Lung Fluid and Phospholipids, International Journal of Pharmaceutics 217 (2001) 25-31.

Moghimi, S. Moein et al., "Recognition by Macrophages and Liver Cells of Opsonized Phospholipid Vesicles and Phospholipid Headgroups", 18(1) Pharmaceutical Res, pp. 1-8 (2001).

Molina, M. C. et al., "The Stability of Lyophilized Lipid/DNA Complexes During Prolonged Storage," J. Pharm. Sci. 93(9):2259-2273, abstract only, one page, [on-line] [retrieved Sep. 2005] Retrieved from the Internet, (2004).

Monnier et al., *Mechanisms of Protection Against Damage Mediated by the Maillard Reaction in Aging Gerontology* 37:152-165 (1991).

Morel, et al., "Crossregulation between Th1 and Th2 cells", Critical Reviews in Immunology U.S., 1998, pp. 275-303, vol. 18, No. 4.

Mouradian, R. et al., "Degradation of Functional Integrity During Long-Term. Storage of a Freeze-Dried. Biological Membrane", Cryobiology 22: 119-127 (1985).

Moynihan et al., "Dependence of the Glass Transition Temperature on Heating and Cooling Rate", J. Physical. Chem. 78(26):2673-2677 (1974).

Muller, et al., "On the Influence of Molecular Forces on the Deformation of an Elastic Sphere and It's Sticking to a Rigid Plane", *J. Colloid Interface Sci.*, 77: 91 (1980).

Mumenthaler, M. et al., "Feasibility Study on Spray-Drying Protein Pharmaceuticals: Recombinant Human Growth Hormone and Tissue-Type Plasminogen Activator," *Clinical Research* 11(1): 12-20 (1994).

Murphy, B. R. et al., "Chapter 19: Immunization Against Viruses", in *Fields of Virology*, 2nd Edition, vol. 1, Raven Press, pp. 469-502 (1990).

Murphy, Brian R. et al., *Fields Virology*, vol. 1, Chapter 16, *Immunization Against Virus Disease*, 467, at page 468, first full paragraph, first column, lines 26-33 (Bernard N. Fields et al. eds., Lippincott-Raven Publishers, 3rd ed. 1996).

Mutterlein, et al., "New Technology for Generating Inhalation Aerosols—Preliminary Results with the Piezoelectrical Pocket-Inhaler", *J. Aerosol Med.*, 1: 231 (1988).

Nabel, G. J. et al., "Direct Gene Transfer With DNA-Liposome Complexes in Melanoma," Proc. Nat. Acad. Sci. 90:11307-11311 (1993).

Nabel, G. J. et al., "Immunotherapy of Malignancy by In Vivo Gene Transfer Into Tumors," *Hum. Gene. Ther*. 3(4): 3 99-4 10 (Aug. 1992) Abstract only [on-line].

Naini, V. et al., "Particles for Inhalation Produced by Spray Drying and Electrostatic Precipitation of Different Protein-Sugar Solutions". *Respiratory Drug Delivery V*, pp. 382-384 (1996).

Naini, V. et al., "Physicochemical Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Natarajan, P., Crystallization Conditions for VIPER Entries [on-line] [retrieved Nov. 4, 2004] Retrieved from the Internet 5 pages (last updated Jan. 3, 2002).

Nektar Notice of Opposition against EP 939622 B1 (May 12, 2003).

Nektar U.S. Appl. No. 08/044,358, "Compositions and Methods for Nucleic Acid Delivery to the Lung" filed by Patton et al. on Apr. 7, 1993, assigned to Inhale Therapeutic Systems.

Newman, "Ovalbumin peptide encapsulated in poly(d,l lactic-co-glycolic acid) microspheres is capable of inducing a T helper type 1 immune response", J. Cont. Rel., p. 49-59.

Niven, R. W., "Delivery of Biotherapeutics by Inhalation Aerosol," *Critical Reviews in Therapeutic Drug Carrier Systems*, 12(2&3):151-231 (1995).

Niven, R. W., "Delivery of Biotherapeutics by Inhalation Aerosols," *Pharmaceutical Technology* 72-75, 80 (Jul. 1993).

Nornerg, J. et al., "Glass Transition in DNA From Molecular Dynamics Simulation", *Proc. Natl. Acad. Sci. USA* 93:10173-10176 (1996).

Notter, R.H., "Physical Chemistry and Physiological Activity of Pulmonary Surfactants", In: Surfactant Replacement therapy (Eds. Shapiro and Notter, Alan R. Liss, Inc., New York), Chapter 2, pp. 19-71 (1989).

Odegard, P. S. et al., "Inhaled Insulin: Exubera", *The Annals of Pharmacotherapy* 39:843-853 (2005).

Ohtake, S. et al., "Effect of pH, Counter Ion and Phosphate Concentration on the Glass Transition Temperature of Freeze-Dried Sugar-Phosphate Mixtures", *Pharmaceutica Research* 21(9):1615-1621(2004).

Okamoto, H. et al., "Dry Powders for Pulmonary Delivery of Peptides and Proteins", *Kona* 20:71-83 (2002).

Oksanen et al., "The Relationship between the Glass Transition Temperature and Water Vapor Absorption by Poly(Vinylpyrrolidone)," *Pharmaceutical Research* 7(6): 654-657 and errata on p. 974(1990).

Okumura, K. et al., "Intratracheal Delivery of Calcitonin Dry Powder in Rats and Human Volunteers," S.T.P. *Pharmaceutical Sciences* 4(I):5 pages (Jan. Feb. 1994).

Onodera et al., "Glass Transition of Dehydrated Amorphous Solid", *Bull. Chem. Soc.* Japan 41(9):222 (1968).

Opposition Papers of European Patent No. EP 1019021 (European Application No. 98950826.2) Dated: Jun. 3, 2004 through Nov. 15, 2006.

Owens, D. R. et al., "Alternative Routes of Insulin Delivery," *Diabetic Medicine* 20:886-898 (2003).

Pacheco-Soares, et al., "Phagocytosis of Enteropathogenic *Escherichia coli* and *Candida albicans* by Lectin-like receptors", Braz. J. Med. Biol. Res., 25:1015-1024, 1992.

Palmer, K.J., et al., "X-Ray Diffractometer and Microscopic Investigation of Crystallization of Amorphous Sucrose", Agricultural and Food Chemistry 4(1): 77-81 (Jan. 1956).
Parasassi et al. "Calcium-Induced Phase Separation in Phospholipid Bilayers. A Fluorescence Arisotropy" Cellular and Molecul Bio 32(3): 261-266 (1986).
Parks, "Studies on Glass. II The Transition Between the Glassy and Liquid States in the Case of Glucose", *Journal of Physical Chemistry* 1366-1379 (1928).
Patel, M. M. et al., "Degradation Kinetics of High Molecular Weight Poly(L Lactide) Microspheres and Release Mechanism of Lipid: DNA Complexes", *Journal of Pharmaceutical Sciences*, 93(10): 2573-2584 (2004).
Patton, John S. et al., "Inhaled Insulin", 35 Advanced Drug Delivery Reviews, pp. 235-247 (1999).
Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).
Pekarek et al. "Double-walled polymer microspheres for controlled drug release," Nature 367:258-260 (1994).
Persson, G. and J.E. Wiren, The bronchodilator response from inhaled terbutaline is influenced by the mass of small particles: a study on a dry powder inhaler (Turbuhalter) Eur. Respir J. 2:253-256 (1989).
Phillips, E. et al., "Size Reduction of Peptides and Proteins by Jet-Milling", Respiratory Drug Delivery VI, pp. 161-167 (1998).
Pikal et al., "Thermal Decomposition of Amorphous I3-Lactam Antibacterials", *Journal of Pharmaceutical Science* 66(9): 1312-1316 (Sep. 1997).
Pikal, M. J. et al., "The Stability of Insulin in Crystalline and Amorphous Solids: Observation of Greater Stability for the Amorphous Form", *Pharmaceutical Research* 14(10):1379-1387 (1997).
Pikal, M. J. et al., Errata of "The Stability of Insulin in Crystalline and Amorphous Solids: Observation of Greater Stability for the Amorphous Form," *Pharmaceutical Research* 15(2):362-363 (1998).
Pikal, M. J., "Freeze-Drying of Proteins Part II: Formulation Selections," Biopharm 3(8):26-30 (Oct. 1990).
Pine, S. H. et al., "15-3 Oligoaccharides and Polysaccharides," *Organic Chemistry*, 4a'edition. McGraw-Hill International Book Company, p. 763 (1980).
Pisecky, J., "2. Evaporation and Membrane Filtration", *Handbook of Milk Powder Manufacture*, Niro A/S, Denmark, p. 3 (1997).
Pocchiari, M. et al., "Amphotericin B: A Novel Class of Antiscrapie Drugs," J Infect. Dis. 160(5):795-802 (Nov. 1989).
Prestrelski, S. J. el al., "Optimization of Lyophilization Conditions for Recombinant Human Interleukin-2 by Dried-State Conformational Analysis Using Fourier-Transform Infrared Spectroscopy," *Pharmaceutical Research* 12(9):1250-1259 (1995).
Prestrelski, S. J. et al., "Separation of Freezing- and Drying-Induced Denaturation of Lyophilized Proteins Using Stress-Specific Stabilization," *Archives of Biochemistry and Biophysics* 303(2) :465-473 (Jun. 1993).
Prigozy, et al., "The mannose receptor delivers lipoglycan antigens to endosomes for presentation to T cells by CD1b molecules", Immunity, 6:187-197, 1997.
Product Sheet for Intal® Inhaler.
Quan, C. Protein Science 4(2): 148, Abstract No, 490-T (1995).
Ramanujam, R. et al., "Ambient-Temperature-Stable Molecular Biology Reagents," *Biotechniques* 14(3):470-473 (1993).
Reboiras, M.D. "Activity Coefficients of CaCl2and MgCl2 in the Presence of Dipalmitoylphosphatidylcholine-Phosphatidylinositol Vesicles in Aqueous Media" Bioelectrochemistry and Bioenergetics 39: 101-108 (1996).
Reise Sousa, et al., "Phagocytosis of antigens by Langerhans cells in vitro", J. Exp. Med., 178:509-517, 1993.
Ringe, D. et al., "The Glass Transition in Protein Dynamics: What it is, Why it Occurs, and How to Exploit It", *Biophys. Chem.* 105(2-3):667-680, Abstract only, [on-line] [retrieved Nov. 19, 2004] Retrieved from the Internet (2003).
Roitt, et al., "Roitt's Essential Immunology 10th Ed.", Blackwell Science, Chapter 20-Autoimmune diseases, 2001, pp. 442 & 449.

Roll, et al., "Perinatal autoimmunity in offspring of diabetic parents. The German Multicenter Baby-Diab study: detection of humoral immune responses to islet antigens in early childhood", Diabetes, 45:967-973, 1996.
Roos, "Phase Transitions of Mixtures of Amorphous Polysaccharides and Sugars," *Biotechnology Progress* 7(1): 49-53 (1991).
Rosen, Surfactants and Interfacial Phenomena, Second Edition, John Wiley & Sons, New York, pp. 326-329 (1989).
Roser, B., "Trehalose Drying: A Novel Replacement for Freeze Drying" *Biopharm* 4:47-53 (1991).
Roser, B., "Trehalose, A New Approach to Premium Dried Foods," *Trends in Food Sci. And Tech.* pp. 166-169 (Jul. 1991).
Roser, et al., "A Sweeter Way to Fresher Food" *New Scientist* pp. 25-28 (May 15, 1993).
Roth, C. et al., "Production of Hollow Spheres," Paragamon Press, vol. 19 (No. 7), p. 939-942, (Feb. 26, 1988).
Royall et al. "Characterisation of Moisture Uptake Effects on the Glass Transitional Behaviour of an Amorphous Drug Using Modulated Temperature DSC" Int. J. Pharm. 192: 39-46 (1999).
Rued, "Enhancement of the Local Immune Response in the Respiratory System by Bacterial Immunomodulators", Regional Immu., p. 361-364.
Sacchetti, et al., "Spray-Drying and Supercritical Fluid Particle Generation Techniques", *Inhalation Aerosols: Physical and Biological Basis for Therapy*, A.J. Hickey, ed., Marcel Dekkar, New York, Chapter 11, p. 337 (1996).
Saleki-Gerhardt, A. et al., "Hydration and Dehydration of Crystalline and Amorphous Forms of Raffinose," *Journal of Pharmaceutical Sciences*, 84(3):318-323 (Mar. 1995).
Saleki-Gerhardt, A. et al., "Non-Isothermal and Isothermal Crystallization of Sucrose From the Amorphous State," *Pharmaceutical Research* 11 (8):1166-1173 (1994).
Sambrook, et al., *Molecular Cloning: A Laboratory Manual*, 2nd. ed., "Concentrating Nucleic Acids: Precipitation with Ethynol or Isopropanol", pp. E.10-E.17, Cold Spring Harbor Laboratory Press (1989).
Sanchez, J. et al., "Recombinant System for Overexpression of Cholera Toxin B Subunit in Vibro Cholerae as a Basis for Vaccine Development" Proc. Natl. Acad. Sci. USA 86:481-485 (1989).
Santinho, Ana J.P., et al., "Influence of Formulation on the Physicochemical Properties of Casein Microparticles", 186 Int. J. of Pharmaceutics, pp. 191-198 (1999).
Sarkar and Moore, "Immunization of Mice Against Murine Mammary Tumor Virus Infection and Mammary Tumor Development," Cancer Research 38:1468-1472 (1978).
Sasaki, et al., "Human immunodeficiency viris type-1 specific immune responses induced by DNA vaccination are greatly enhances by manna-coated DIC14-amidine", Euro. J. of Immunology, Dec. 1997, pp. 3121-3129, vol. 27, No. 12.
Satoh, Koichi, "Determination of Binding Constants of Ca2+, Na+, and Cl- Ions to Liposomal Membranes of Dipalmitaoylphosphatidylcholine at Gel Phase by Particle Electrophoresis", Biochem. Biophys. Acta 1239:239-248 (1995).
Schamblin and Zografi. "Enthalpy Relaxation in Binary Amorphous Mixtures Containing Sucrose" *Pharmaceutical Research* 15(12): 1828-1834 (Dec. 1998).
Schebor, C. et al., "Color Formation Due to Non-Enzymatic Browning in Amorphous, Glassy, Anhydrous, Model Systems", *Food Chemistry* 65:427432 (1999).
Schlesinger, L.S., "Macrophage phagocytosis of virulent but not attenuated strains of *Mycobacterium tuberculosis* is mediated by mannose receptors in addition to complement receptors", J. Immunol., 150:2920-2930, 1993.
Schöler N., et al., "Surfactant, But Not the Size of Solid Lipid Nanoparticles (SLN) Influences Viability And Cytokine Production Of Macrophages", 221 Int. J. of Pharmaceutics pp. 57-67 (2001).
Schram, L. "The Language of Colloid and Interface Science, A Dictionary of Terms", American Chem. Sco. p. 157 (1993).
Schröder, et al., "Influence of Bulk and Tapped Density on the Determination of the Thermal Conductivity of Powders and Blends", AAPS Pharm Sci. Tech, 2007, vol. 8 No. 3, Article 78, pp. E1-E8.

Sciarra et al., "Aerosols", *Remington's Pharmaceutical Sciences*, Chap. 93, 17 Ed., Mack Publishing Company, Alfonso R. Gennaro, editor, pp. 1662-1677 (1985).
Sebhatu, T. et al., "Assessment of the Degree of Disorder in Crystalline Solids by Isothermal Microcalorimetry", *International Journal of Pharmaceutics* 104:135-144 (1994).
Seddon, J.M. "Structure of the Inverted Hexagonal (HII) Phase, and Non-Lamellar Phase Transitions of Lipids" Biochim Biophys Acta 1031:1-69 (1990)., in particular p. 43-44 and 49-50.
Seelig, Joachim Handb. Met. -*Ligand Interact. Biol. Fluids: Bioinorg. Chem.* § Metal Ion Interactions with Lipids: 698-706 (1995).
Sellers, S. P. et al., "Dry Powders of Stable Protein Formulations From Aqueous Solutions Prepared Using Supercritical CO2-Assisted Aerosolization", *Journal of Pharmaceutical Sciences*, 90(6): 785-797 (2001).
Serajuddin, A. T. M. et al. "effect of Thermal History on the Glassy State of Indapamide," J. Pharm. Pharmacol. 38:219-220 (1986).
Shah et al. "The Ionic Structure of Sphingomyelin Monolayers" Biochem Biophys Acta 135: 184-187 (1967).
Shalaev, E. Y. et al., "How Does Residual Water Affect the Solid-State Degradation of Drugs in the Amorphous State", *Journal of Pharmaceutical Sciences*, 85(11): 1137-111 (1996).
Shalaev, E.Y. et al., "Structural Glass Transitions and Thermophysical Processes in Amorphous Carbohydrates and Their Supersaturated Solutions," *J. Chem. Soc. Faraday Trans.* 91(10):1511-1517 (1995).
Sharma, V.K. et al., "Effect of Vacuum Drying on Protein-Mannitol Interactions: the Physical State of Mannitol and Protein Structure in the Dried State", AAPS PharmSciTech 5(1) Article 10:1-12 [on-line] [retrieved] Retrieved from the Internet (2004).
Shavnin et al. "Cholesterol Affects Divalent Cation-Induced Fusion and Isothermal Phase Transitions of Phospholipid Membranes" Biochim Biophys Acta 946: 405-416 (1988).
Shibata, et al., "Chitin Particle-Induced Cell-Mediated Phagocytosis Initiaties IL-12 Production", J. of Immunology, 1997, pp. 2462-2467, vol. 159, No. 5.
Simha et al. "On a General Relation Involving the Glass Temperature and Coefficients of Expansion of Polymers" J. Chem. Physics 37(5): 1003-1007 (Sep. 1962).
Simone, et al., "Immunologic 'vaccination' for the prevention of autoimmune diabetes (type 1A)", Diabetes Care, 22 Supp. 2:B7-B15, 1999.
Singer et al., "Thermotolerance in *Saccharomyces cerevisiae*: the Yin and Yang of Trehalose", *Tibtech* 16:460-468. (1998).
Skrabanja et al., "Lyophilization of Biotechnology Products" *PDA J. Pharm. Sci Technol.* 48(6):311-7 (1994).
Slade and Levine, "The Glassy State Phenomenon in Food Molecules," *The Glassy State in Foods*, Blanshard & Lillford, editors: 35-101 (1993).
Slade and Levine, "Non-Equilibrium Behavior of Small Carbohydrate-Water Systems," Pure and Applied Chemistry, 60(12): 1841-1864 (1988).
Sokolov et al., "Glassy Dynamics in DNA: Ruled by Water of Hydration" *Journal of Chemical Physics* 110(14):7053-7057 (1999).
Sola-Penna, Mauro et al., *Stabilization Against Thermal Inactivation . . . : Why is Trehalose More Effective Than Other Sugars?* 360(1) Archives of Biochemistry and Biophysics 10-14, Article No. BB9809606, (Dec. 1998).
Sonner, C. et al., "Spray-Freeze-Drying for Protein Powder Preparation: Particle Characeterization and a Case Study With Trypsinogen Stability", *Journal of Pharmaceutical Sciences* 91(10):2122-2139 (2002).
SPI Polyols™ "What are Polyols? What do Polyols do? What are Polyols' functionality?", [on-line] [retrieved Jun. 25, 2004] Retrieved from the Internet one page (2003).
Stahl, P.D., "The Mannose Receptor and Other Macrophage Lectins", Curr. Opin. Immunol., 4:49-72, 1992.
Stribling, R. et al., "Aerosol Gene Delivery in Vivo," *Proc. Natl. Acad. Sci*. 89:11277-11281 (Dec. 1992).
Strickley, R. G. et al., "Solid-State Stability of Human Insulin II. Effect of Water on . . . in Lyophiles from pH 2-5 Solutions: Stabilization Against Covalent Dimer Formation", *Journal of Pharmaceutical Sciences* 86(6):645-653 (1997).

Strom, A. R. And Kaasen. L. "Trehalose Metabolism in Escherichia coli: Stress Protection and Stress Regulation of Gene Expression", *Molecular Microbiology* 8(2):205-210 (1993).
Stubberud, L. et al., "The Use of Gravimetry for the Study of the Effect of Additives on the Moisture-Induced Recrystallisation of Amorphous State", *International Journal of Pharmaceutics* 163:145-156 (1998).
Sugisaki et al. "Calorimetric Study of the Glassy State. IV. Heat Capacities of Glassy Water and Cubic Ice" Bulletin of the Chemical Society of Japan 41: 2591-2599 (Nov. 1968).
Sukenik et al., "Enhancement of a Chemical Reaction Rate by Proper Orientation of Reacting Molecules in the Solid State", J. Am. Chem. Soc. 97: 5290-5291 (Sep. 1975).
Sussich, F. et al., "Reversible Dehydration of Trehalose and Anhydrobiosis: From Solution State to an Exotic Crystal?", *Carbohydrate Research* 334: 165-176 (2001).
Swarbrick et al., Encyclopedia of Pharmaceutical Technology 1994, vol. 9, pp. 288-290.
Takahashi et al., "Induction of CD8+cytotoxic T cells by immunization with purified HIV-1 envelope protein in ISCOMs", Nature 344:873-875 (Apr. 1990).
Tarara, T. et al. "Characterization of Suspension-Based Metered Dose Inhaler Formulations Composed of Spray-Dried Budesonide Microcrystals Dispersed in HFA", J. Pharm Res, vol. 21, No. 9, pp. 1607-1614 (Sep. 2004).
Tarelli, E. et al., "Additives to Biological Substances. 111. The Moisture Content and Moisture Uptake of Commonly Used Carrier Agents . . . In the Preperation of International Biological Standards," Journal of Biological Standarization 15:331-340 (1987).
Tatulian, S.A. "Binding of Alkaline-Earth Metal Cations and Some Anions to Phosphatidylcholine Liposomes" Eur. J. Biochem. 170: 413-420 (1987).
Tatulian, S.A. "Evalutation of Divalent Cation Binding to Phosphatidylserine Membranes by an Analysis of Concentration Dependence of Surface Potential" J. Colloid Interface Science 175: 131-137 (1995).
Thatcher, E., "Quantitation of Virus" [on-line] Retrieved from the internet <URL:http://www.sonoma.edu/users/t/thatcher/biol383/lab.htm>, (last updated Jan. 5, 2002).
Timko et al., "Thermal Analysis Studies of Glass Dispersion Systems", *Drug Devel. Ind. Pharm*. 10:425451 (1984).
Timsina, T. et al., "Drug Delivery to the Respiratory Tract Using Dry Powder Inhalers," *International Journal of Pharmaceutics* 101:1-13 (1994).
To et al., "Collapse. A Structural Transition in Freeze Dried Carbohydrates", *J. Fd. Technol.* 13: 567-581 (1978).
Todo, Hirosiki et al., "Effect of Additives on Insulin Absorption From Intratracheally Administered Dry Powders in Rats", 220 Int. J. of Pharmaceutics pp. 101-110 (1999).
Toyama, A. (ed) *Handbook of Natural Product for food processing*, 9th Edition, Osaka, Japan, Shokuhin to Kagaku Sha, pp. 384 and 495 (ISBN4-87994-048-8), (1986).
Trolle, S. et al., "In Vivo Fate and Immune Pulmonary Response After Nasal Administration of Microspheres Loaded with Phosphorylcholine-Thyroglobulin", 183 Int. J. of Pharmaceutics pp. 73-79 (1999).
Tsouroufis, S. et al., "Loss of Structure in Freeze-Dried Carbohydrates Solutions: Effect of Temperature, Moisture Content and Composition", J. Sci. Fd. Agric. 27:509-519 (1976).
Ulrich, "Biophysical Aspects of Using Liposomes as Delivery Vehicles", *Bioscience Reports* 22(2):129-150 (2002).
Underwood et al., "A Novel Technique for the Administration of Bronchodilator Drugs Formulated as Dry Powders to the Anaesthetized Guinea Pig", *J. of Pharmacological Methods*, vol. 26, pp. 203-210, 1991.
Uritani, M. et al., "Protective Effect of Disaccharides on Restriction Endonucleases During Drying Under Vacuum." *J. Biochem.* 117:774-779 (1995).
Vain et al., "Development of the particle inflow gun", *Plant Cell, Tissue and Organ Culture* 33:237-246 (1993).
Vavelyuk, O.L. et al., "Thermostability of DNA and Its Association with Vitrification", *Tsitologiya* 41(11):958-965 (1999).

Verstraeten et al. "Effects of Al(3+) and Related Metals on Membrane Phase State and Hydration: Correlation with Lipid Oxidation" Arch Biochem Biophys 375(2): 340-346 (Mar. 15, 2000).

Vidgren, M. T. et al., "Comparison of Physical and Inhalation Properties of Spray-Dried and Mechanically Micronized Disodium Cromoglycate," International Journal of Pharmaceutics 35:139-144 (1987).

Vromans, H. et al., "Studies on Tableting Properties of Lactose. VII. The Effect of Variations in Primary Particle Size and Percentage of Amorphous Lactose in Spray Dried Lactose Products," International Journal of Pharmaceuticc 35:29-36 (1987).

Wang, et al., eds. *Stability and characterization of protein and peptide drugs*, Table of Contents, 6 pages (1993).

Weers, "Colloidal Particles in Drug Delivery," Current Opinion in Colloid & Interface Science (1998), 3:540-544.

Welsh, D. T., "The Role of Compatible Solutes in the Adaptation and Survival of *Escherichia coli*," Ph.D. Thesis Submitted to Department of Biological Sciences, Univeristy of Dundee. pp. 1-262. (Aug. 1992).

Whipps et al. "Growth of Calcium Monohydrate at Phospholipid Langmuir Monolayers" J Cryst Growth 192: 243-249 (1998).

Whittier, E., "Lactose and its Utilization: A Review," *J. Dairy Sci.* 27(7)505-537 (Jul. 1994).

William and Leopold, "The Glassy State in Corn Embryos" Plant Physiology 89:977-981 (1979).

Williams et al., "The Temperature Dependence of Relaxation Mechanisms in Amorphous Polymers and Other Glass Forming Liquids", The Journal of the American Chemical Society 77: 3701-3707 (1955).

Williams III, R.O., et al., "Formulation of a Protein with Propellant HFA 134a for Aerosol Delivery", 7 European J. of Pharmaceutical Sciences, pp. 137-144 (1998).

Wilson and Pearson, "Evidence that *Leishmania donovani* utilizes a mannose receptor on human mononuclear phagocytes to establish intracellular parasitism", J. Immunol., 136:4681-4688, 1986.

Wolff, J. A. et al., "Grafting Fibroblasts Genetically Modified to Produce L-Dopa in a Rat Model of Parkinson Disease," Proc. Natl. Acad. Sci. 86:9011-9014 (Nov. 1989).

Xi, Y. G. et al., "Amphotericin B Treatment Dissociates in Vivo Replication of the Scrapie Agent From PrP Acummulation", *Nature* 356:598-601 (Apr. 1992).

Yamaguchi et al. "Adsorption of Divalent Cations onto the Membrane Surface of Lipid Emulsion" Colloids and Surfaces B: Biointerfaces 5: 49-55 (1995).

Yamamoto, et al., "Involvement of mannose receptor in cytokine interleukin-1 beta (IL- 1 beta), IL-6, and granulocyte-macrophage colony-stimulating factor responses, but not in chemokine macrophage inflammatory protein 1 beta (MIP-1beta), MIP-2, and KC responses, caused by attachment of Candida albicans to macrophages", Infect. Immun., 65:1077-1082, 1997.

York, "Powdered Raw Materials: Characterizing Batch Uniformity," *Respiratory Drug Delivery IV, Programs and Proceedings*, edited by Byron, Dalby and Farr: 83-91 (1994).

Yoshida, H. et al., "Absorption of Insulin Delivered to Rabbit Trachea Using Aerosol Dosage Form," Journal of Pharmaceutical Sciences 68(5): 670 (May 1979).

Yoshinari, T. et al., "Moisture Induced Polymorphic Transition of Mannitol and its Morphological Transformation", *International Journal of Pharmaceutics*, 247:69-77 (2002).

Yoshioka, M. et al., "Crystallisation of Indomethacin From the Amorphous State Below and Above Its Glass Transition Membrane," *Journal of Pharmaceutical Sciences* 83(12):1700-1705 (Dec. 1994).

Zarif et al., "Amphotericin B. Cochleates as a Novel Oral Delivery System," International Symposium, p. 965-965 (1999).

Zubay, G. Biochemistry, Second Edition, pp. 211-256 "Nucleotides and Nucleic Acids" (1988).

Zubay, G. Biochemistry, Second Edition, pp. 39 & 169, Table 5-6 Major Steroid Hormones (1988).

Office Action in U.S. Appl. No. 10/750,934 dated Jan. 15, 2009.
Office Action in U.S. Appl. No. 10/750,934 dated Dec. 28, 2007.
Office Action in U.S. Appl. No. 10/750,934 dated May 11, 2007.
Office Action in U.S. Appl. No. 10/750,934 dated Jun. 25, 2009.
Office Action in U.S. Appl. No. 10/750,934 dated Sep. 10, 2008.

\* cited by examiner

FORMULATION FOR PULMONARY ADMINISTRATION OF ANTIFUNGAL AGENTS, AND ASSOCIATED METHODS OF MANUFACTURE AND USE

CROSS-REFERENCE TO RELATED APPLICATIONS

This application is a continuation-in-part of:

U.S. patent application Ser. No. 10/032,239, filed Dec. 21, 2001, which claims priority under 35 U.S.C. §119(e)(1) to provisional U.S. Patent Application Ser. No. 60/257,613, filed Dec. 21, 2000;

U.S. patent application Ser. No. 09/851,226, filed May 8, 2001, which claims priority under 35 U.S.C. §119(e)(1) to provisional U.S. Patent Application Ser. Nos. 60/208,896, filed Jun. 2, 2000, and 60/216,621, filed Jul. 7, 2000, and which is a continuation-in-part of U.S. Ser. No. 09/568,818, filed May 10, 2000;

U.S. patent application Ser. No. 10/750,934, filed Dec. 31, 2003, which claims priority under 35 U.S.C. §119(e)(1) to provisional U.S. Patent Application Ser. No. 60/437,210, filed Dec. 31, 2002;

U.S. patent application Ser. No. 09/888,311, filed Jun. 22, 2001, which claims priority under 35 U.S.C. §119(e)(1) to provisional U.S. Patent Application Ser. No. 60/216,621, filed Jul. 7, 2000;

U.S. patent application Ser. No. 10/751,342, filed Dec. 31, 2003, which claims priority under 35 U.S.C. §119(e)(1) to provisional U.S. Patent Application Ser. No. 60/437,363, filed Dec. 31, 2002; and U.S. patent application Ser. No. 11/158,332, filed Jun. 21, 2005, which claims priority under 35 U.S.C. §119(e)(1) to provisional U.S. Patent Application Ser. No. 60/581,586, filed Jun. 21, 2004.

The disclosures of each of the aforementioned patent applications are incorporated by reference in their entireties.

TECHNICAL FIELD

This invention relates generally to pulmonary drug delivery, and more particularly relates to particulate formulations for the pulmonary administration of an antifungal agent such as amphotericin B. The invention has utility in the fields of drug delivery, pharmaceutical formulation, and medicine.

BACKGROUND

Pulmonary fungal infections, such as invasive filamentous pulmonary fungal infection (IFPFI), are major causes of morbidity and mortality in immunocompromised patients. The immune system of an individual may be compromised by some diseases, such as human immunodeficiency acquired immunodeficiency syndrome (AIDS) and systemic lupus erythematosus (SLE), and/or may be deliberately compromised by immunosuppressive therapy. Immunosuppressive therapy is often administered to patients undergoing cancer treatments and/or patients undergoing a transplant procedure. Immunocompromised patients have an increased susceptibility to pulmonary fungal infections. Severely immunocompromised patients, e.g., patients with prolonged neutropenia and patients requiring long-term prednisone therapy, are particularly susceptible to pulmonary and/or nasal fungal infection.

The most common pulmonary fungal infection in immunocompromised patients is pulmonary aspergillosis. Aspergillosis is a disease caused by *Aspergillus* fungal species (*Aspergillus* spp.), which invades the body primarily through the lungs. Most commonly, aspergillosis is due to infection with *Aspergillus fumigatus, Aspergillus flavus, Aspergillus niger, Aspergillus nidulans*, or *Aspergillus terreus*). Fungal infections of the lung which are caused by *Aspergillus* include, for example, fungal pneumonia and allergic bronchopulmonary aspergillosis. Other filamentous and dimorphic fungi can lead to pulmonary infections as well. These additional mycotic pathogens are usually endemic and include, for example, blastomycosis, disseminated candidiasis, coccidioidomycosis, paracoccidioidomycosis, cryptococcosis, histoplasmosis, mucormycosis, and sporotrichosis, pseudallescheriasis, and pneumocsystis carinii. Though typically not affecting the pulmonary system, infections caused by *Candida* spp., which are usually systemic and most often result from infections via an indwelling device or IV catheter, wound, or a contaminated solid organ transplant, account for 50 to 67% of total fungal infections in immunocompromised patients.

Amphotericin B is the only approved fungicidal compound currently used to treat aspergillosis and is generally delivered intravenously. Amphotericin B is an amphoteric polyene macrolide obtained from a strain of *Streptomyces nodosus*. In its commercial form, amphotericin B is present in both amorphous and crystalline forms. Amphotericin B formulated with sodium desoxycholate was the first parental amphotericin B preparation to be marketed. Systemic intravenous therapies are constrained by dose-dependent toxicities, such as renal toxicity and hepatotoxicity, which hamper the effectiveness of the treatment and lessen the desirability of prophylactic use of amphotericin B. Even with the approved therapy, aspergillosis incidence is rising and estimated to cause mortality in more than 50% of those infected who receive treatment.

There are numerous additional drawbacks associated with prior formulations and methods for administration of amphotericin B to treat pulmonary infections. For instance, prior efforts to prepare amphotericin B formulations for pulmonary delivery have resulted in formulations exhibiting inadequate delivery efficiency, particularly with respect to delivery to the lung per se. That is, a substantial fraction of the drug was delivered systemically rather than locally, as is desirable in the treatment of a lung infection. Shelf life has also been problematic, as has the dependence of lung deposition on peak inspiratory flow rate.

There remains a need in the art for a safe and effective method and formulation for administering amphotericin B and other antifungal agents, particularly polyene antifungal agents, to the lungs. Ideally, systemic delivery should be minimized while delivery to the affected tissues of the lung should be maximized, and there should not be any significant dependence of the amount of drug delivered to the lungs on inspiratory flow rate. An ideal formulation would also exhibit long-term stability and be administrable using different types of dosage forms and/or delivery devices.

SUMMARY OF THE INVENTION

The present invention is directed to the aforementioned need in the art, and, in one embodiment, provides a pharmaceutical formulation for pulmonary administration, comprising a plurality of particulates having a mass median diameter less than 20 μm, wherein each particulate comprises: (a) a lipid matrix; and (b) at least one particle of an active agent in the lipid matrix, wherein the active agent has an aqueous solubility of less than 1.0 mg/ml and at least 90% of the active agent particles in the formulation have a geometric diameter less than 3 μm.

In another embodiment, the invention provides a method for administering an active agent to the lungs of a patient, comprising activating a dry powder inhaler to emit a dose of a pharmaceutical formulation that comprises a plurality of particulates having a mass median aerodynamic diameter of less than 5 μm and a bulk density of less than 0.5 g/cm$^3$, each particulate comprising a lipid matrix and at least one particle of the active agent in the lipid matrix, wherein the dose is inhaled by the patient and inhalation of the dose by the patient provides a $T_{max}$ within 15 minutes of inhalation.

In a further embodiment, a method is provided for treating a patient suffering from a fungal infection of the lung, comprising administering an aerosolized formulation of an antifungal agent to the patient in an amount sufficient to maintain a target lung concentration of the antifungal agent that is at least twice the minimum inhibitory concentration of the antifungal agent, for at least one week.

In an additional embodiment, a method is provided for manufacturing a particulate amphotericin B formulation for pulmonary administration, the method comprising:

(a) mixing a phospholipid, amphotericin B particles each having an initial geometric diameter, and a solvent, to form a suspension;

(b) homogenizing the suspension to form solvent-containing particulates in which the geometric diameter of the amphotericin B particles is less than or equal to the initial geometric diameter; and (c) spray-drying the particulates at a temperature effective to remove the solvent from the microparticles and thereby provide dry formulation particulates of the phospholipid and amphotericin B.

DETAILED DESCRIPTION OF THE INVENTION

Unless otherwise indicated, the invention is not limited to specific formulations, administration regimens, drug delivery devices, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an active agent" includes not only a single active agent but also a combination or mixture of two or more different active agents, reference to "a lipid" includes a single phospholipid as well as two or more phospholipids in combination or admixture, and the like.

As used herein, the term "particle" refers to a discrete microparticle of the active agent per se. By contrast, the term "particulate" refers to a discrete unit of the formulation of the invention, and thus includes a lipid matrix containing at least one active agent "particle," and will typically include at least one additional component as well, e.g., a polyvalent cation. The formulation particulates can assume various shapes and forms (such as hollow and/or porous microstructures) and may include or define voids, pores, defects, interstitial spaces, apertures, and/or perforations, may be spherical, collapsed, deformed, or fractured.

When referring to an active agent, the term encompasses not only the specified molecular entity, but also its pharmaceutically acceptable, pharmacologically active analogs, including, but not limited to, salts, esters, amides, hydrazides, N-alkyl derivatives, N-acyl derivatives, prodrugs, active metabolites, and conjugates. As an example, therefore, the term "amphotericin B" as used herein refers to amphotericin B per se or an analog of amphotericin B as just described.

As used herein, the terms "treating" and "treatment" refer to reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein includes prevention of a particular condition, disease, or disorder in a susceptible individual as well as treatment of a clinically symptomatic individual.

As used herein, "effective amount" refers to an amount covering both therapeutically effective amounts and prophylactically effective amounts.

As used herein, a "therapeutically effective amount" of an active agent refers to an amount that is effective to achieve a desired therapeutic result. A therapeutically effective amount of a given active agent will typically vary with respect to factors such as the type and severity of the disorder or disease being treated and the age, gender, and weight of the patient. Unless otherwise specified, the term "therapeutically effective amount" includes a "prophylactically effective amount," i.e., an amount of active agent that is effective to prevent the onset or recurrence of particular condition, disease, or disorder in a susceptible individual.

As used herein, "mass median diameter" or "MMD" refers to the median diameter of a plurality of particles, typically in a polydisperse particle population, i.e., a population of particles in which there is a range of particle sizes. MMD values as reported herein are determined by laser diffraction (Sympatec Helos, Clausthal-Zellerfeld, Germany) unless the context indicates otherwise. The determination typically involves direct addition of powder samples to the feeder funnel of a Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, the terms "diameter" and "geometric diameter" are used interchangeably to refer to the diameter of a single microparticle (as may be determined by microscopy), which may be an active agent particle or a formulation particulate as those terms are defined above.

As used herein, "mass median aerodynamic diameter" or "MMAD" refers to the median aerodynamic size of a plurality of particles or particulates, typically in a polydisperse population. The "aerodynamic diameter" is the diameter of a unit density sphere having the same settling velocity, generally in air, as a powder and is therefore a useful way to characterize an aerosolized powder or other dispersed particle or particulate formulation in terms of its settling behavior. The aerodynamic diameter encompasses particle or particulate shape, density, and physical size of the particle or particulate. As used herein, MMAD refers to the median of the aerodynamic particle or particulate size distribution of an aerosolized powder as determined by cascade impaction, unless the context indicates otherwise.

As used herein, the term "emitted dose" or "ED" refers to an indication of the delivery of dry powder from an inhaler device after an actuation or dispersion event from a powder unit or reservoir. ED is defined as the ratio of the dose delivered by an inhaler device to the nominal dose (i.e., to the mass of powder per unit dose placed into a suitable inhaler device prior to firing). The ED is an experimentally determined amount, and may be determined using an in vitro system that mimics patient dosing. To determine an ED value, as that term is used herein, a nominal dose of dry powder is placed into a Turbospin® DPI device (PH&T, Italy), described in U.S. Pat. Nos. 4,069,819 and 4,995,385, which are incorporated herein by reference in their entireties. The Turbospin® DPI is actuated, dispersing the powder. The resulting aerosol cloud is then drawn from the device by vacuum (30 L/min) for 2.5 seconds after actuation, at which point it is captured on a tared glass fiber filter (Gelman, 47 mm diameter) attached to the device mouthpiece. The amount of powder that reaches the filter constitutes the delivered dose. For example, for a capsule containing 5 mg of dry powder, capture of 4 mg of powder on the tared filter would indicate an ED of 80% [=4 mg (delivered dose)/5 mg (nominal dose)].

By a "pharmaceutically acceptable" or "ophthalmologically acceptable" component is meant a component that is not biologically or otherwise undesirable, i.e., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

In a first embodiment, a pharmaceutical formulation for pulmonary administration is provided that comprises a plurality of particulates having a mass median diameter less than 20 µm, preferably less than 10 µm, and optimally less than 5 µm, wherein each particulate comprises: (a) a lipid matrix, preferably composed of a phospholipid; and (b) at least one particle of an active agent in the lipid matrix, the active agent having an aqueous solubility of less than 1.0 mg/ml, wherein at least 90% and preferably at least 95% of the active agent particles in the formulation have a geometric diameter less than 3 µm. The active agent is preferably an antifungal agent, e.g., a polyene antifungal agent such as amphotericin B. A detailed description of this embodiment of the invention is provided in the priority applications hereto, incorporated by reference above, particularly U.S. patent application Ser. No. 10/750,934, filed Dec. 31, 2003.

In another embodiment, a method is provided for treating a patient suffering from a fungal infection of the lung, e,g., pulmonary aspergillosis, the method comprising administering to the patient a therapeutically effective amount of the pharmaceutical formulation described above, wherein the formulation is administered via inhalation. A detailed description of this embodiment of the invention is provided in the priority applications hereto, incorporated by reference above, particularly U.S. patent application Ser. No. 10/750,934, filed Dec. 31, 2003.

In a further embodiment, a method is provided for administering an active agent to the lungs of a patient, comprising activating a dry powder inhaler to emit a dose of a pharmaceutical formulation that comprises a plurality of particulates having a mass median aerodynamic diameter of less than 5 µm and a bulk density of less than 0.5 g/cm$^3$, each particulate comprising a lipid matrix and at least one particle of the active agent in the lipid matrix, wherein the dose is inhaled by the patient and inhalation of the dose by the patient provides a $T_{max}$ within 15 minutes of inhalation. A detailed description of this embodiment of the invention is provided in the priority applications hereto, incorporated by reference above, particularly U.S. patent application Ser. No. 10/751,342, filed Dec. 31, 2003.

In another embodiment, the invention provides a method for manufacturing a particulate amphotericin B formulation for pulmonary administration, the method comprising:

(a) mixing a phospholipid, amphotericin B particles each having an initial geometric diameter, and a solvent, to form a suspension;

(b) homogenizing the suspension to form solvent-containing particulates in which the geometric diameter of the amphotericin B particles is less than or equal to the initial geometric diameter; and (c) spray-drying the particulates at a temperature effective to remove the solvent from the microparticles and thereby provide dry formulation particulates of the phospholipid and amphotericin B.

A detailed description of this embodiment of the invention is provided in the priority applications hereto, incorporated by reference above, particularly U.S. patent application Ser. No. 10/750,934, filed Dec. 31, 2003.

It should be noted that the examples and figures of the priority applications are included herein by virtue of those applications standing incorporated by reference into this disclosure. The examples and figures of the priority applications hereto are incorporated by reference herein for all purposes. It should also be noted that certain embodiments of the invention may include combinations of subject matter disclosed in the applications to which the present application claims priority.

We claim:

1. A pharmaceutical formulation for pulmonary administration, comprising a plurality of particulates having a mass median diameter less than 20 µm, wherein each particulate comprises: (a) a lipid matrix; and (b) at least one particle of an active agent in the lipid matrix, said active agent having an aqueous solubility of less than 1.0 mg/ml, wherein at least 90% of the active agent particles in the formulation have a geometric diameter less than 3 µm.

2. The pharmaceutical formulation of claim 1 wherein the plurality of particulates has a mass median diameter less than 10 µm.

3. The pharmaceutical formulation of claim 2, wherein the plurality of particulates has a mass median diameter less than 5 µm.

4. The pharmaceutical formulation of claim 1, wherein at least at least 95% of the active agent particles have a geometric diameter less than 3 µm.

5. The pharmaceutical formulation of claim 4, wherein at least 50% of the active agent particles have a geometric diameter between 0.5 µm and 3 µm.

6. The pharmaceutical formulation of claim 5, wherein at least 50% of the active agent particles have a geometric diameter between 1 µm and 3 µm.

7. The pharmaceutical formulation of claim 1, wherein the lipid matrix comprises a phospholipid.

8. The pharmaceutical formulation of claim 7, wherein the phospholipid has a gel to liquid phase transition temperature greater than about 40° C.

9. The pharmaceutical formulation of claim 8, wherein the phospholipid has a gel to liquid phase transition temperature greater than about 60° C.

10. The pharmaceutical formulation of claim 9, wherein the phospholipid has a gel to liquid phase transition temperature greater than about 80° C.

11. The pharmaceutical formulation of claim 7, wherein the phospholipid is a phosphoglyceride.

12. The pharmaceutical formulation of claim 7, wherein the phospholipid is a saturated phospholipid.

13. The pharmaceutical formulation of claim 7, wherein the particulates further include a polyvalent cation effective to increase the gel-to-liquid transition temperature of the phospholipid.

14. The pharmaceutical formulation of claim 1, wherein the particulates further include a polyvalent cation.

15. The pharmaceutical formulation of claim 14, wherein the polyvalent cation is a divalent cation.

16. The pharmaceutical formulation of claim 15, wherein the divalent cation is $Ca^{2+}$, $Mg^{2+}$, or $Zn^{2+}$.

17. The pharmaceutical formulation of claim 1, wherein the active agent is an antifungal agent.

18. The pharmaceutical formulation of claim 17, wherein the antifungal agent is a polyene.

19. The pharmaceutical formulation of claim 18, wherein the antifungal agent is selected from ambruticin, amphotericin B, hamycin, natamycin, nystatin, and pimaricin.

20. The pharmaceutical formulation of claim 19, wherein the antifungal agent is amphotericin B.

21. The pharmaceutical formulation of claim 1, further including particles of the active agent that are not incorporated in the particulates.

* * * * *